(12) United States Patent
Clarot et al.

(10) Patent No.: US 9,034,401 B1
(45) Date of Patent: May 19, 2015

(54) PHARMACEUTICAL COMPOSITIONS COMPRISING PLANT EXTRACTS AND METHODS FOR REDUCING DURATION OF A COMMON COLD USING SAME

(71) Applicant: Matrixx Initiatives, Inc., Scottsdale, AZ (US)

(72) Inventors: Timothy L. Clarot, Phoenix, AZ (US); Arlene M. Ascarate, Gilbert, AZ (US)

(73) Assignee: MATRIXX INITIATIVES, INC., Scottsdale, AZ (US)

( * ) Notice: Subject to any disclaimer, the term of this patent is extended or adjusted under 35 U.S.C. 154(b) by 0 days.

(21) Appl. No.: 14/327,339

(22) Filed: Jul. 9, 2014

Related U.S. Application Data

(60) Provisional application No. 61/930,881, filed on Jan. 23, 2014.

(51) Int. Cl.
*A61K 36/42* (2006.01)
*A61K 36/896* (2006.01)
*A61K 36/00* (2006.01)
*A61K 36/515* (2006.01)
*A61K 36/30* (2006.01)

(52) U.S. Cl.
CPC ............... *A61K 36/515* (2013.01); *A61K 36/42* (2013.01); *A61K 36/30* (2013.01)

(58) Field of Classification Search
CPC .............................. A61K 36/42; A61K 36/896
See application file for complete search history.

(56) References Cited

U.S. PATENT DOCUMENTS

| | | |
|---|---|---|
| 1,086,900 A | 2/1914 | David |
| 2,726,188 A | 12/1955 | Allison |
| 4,956,385 A | 9/1990 | Eby, III |
| RE33,465 E | 11/1990 | Eby, III |
| 5,260,335 A | 11/1993 | Wagner et al. |
| 5,409,905 A | 4/1995 | Eby, III |
| 5,785,988 A | 7/1998 | Fust |
| 5,908,611 A | 6/1999 | Gottlieb et al. |
| 5,939,071 A | 8/1999 | Joseph |
| 6,083,525 A | 7/2000 | Fust |
| 6,187,332 B1 | 2/2001 | Gern et al. |
| 6,344,210 B2 | 2/2002 | Fust |
| 6,365,624 B1 | 4/2002 | Davidson |
| 6,528,081 B1 | 3/2003 | Zellner |
| 6,572,849 B2 | 6/2003 | Shahinian, Jr. |
| 6,641,801 B1 | 11/2003 | Brown |
| 6,841,146 B2 | 1/2005 | Haslwanter et al. |
| 7,029,705 B2 | 4/2006 | Fuhr |
| 7,541,052 B1 | 6/2009 | Cordray |
| 7,671,086 B2 | 3/2010 | Berg |
| 7,754,763 B2 | 7/2010 | Clarot |
| 8,337,906 B2 | 12/2012 | Zinreich et al. |
| 2003/0185763 A1 | 10/2003 | Haslwanter et al. |
| 2007/0082071 A1 | 4/2007 | Willimann |
| 2007/0110676 A1 | 5/2007 | Clymer et al. |
| 2011/0244041 A1 | 10/2011 | Popp |
| 2012/0263805 A1 | 10/2012 | Popp |
| 2013/0216574 A1 | 8/2013 | Liu |

OTHER PUBLICATIONS

Champney et al. (1974) J. Pharma. Sci. vol. 63, No. 6, pp. 942-943.*
Glatthaar-Saalmuller et al. (2001) Forsch Komplementarmed. Klass Naturheilkd. 8: 207-212.*
Herrera-Ruiz et al. (2006) Phytomedicine 13, 23-28.*
Kanchanapoom et al. (2002) Chem. Pharm. Bull. 50(6): 863-865.*
Revilla et al. (1998) J. Agric. Food Chem. 46, 4592-4597.*
Zang et al. (1997) J. Agric. Food Chem. 45, 1758-1761.*
Similasan web page printout for Nasal Allergy Relief Preservative Free Nasal Mist, http://www.similasanusa.com/nasal-allergy-relief, 2010/13.

* cited by examiner

*Primary Examiner* — Chris R Tate
*Assistant Examiner* — Russell Fiebig
(74) *Attorney, Agent, or Firm* — Snell & Wilmer L.L.P.

(57) ABSTRACT

The present disclosure describes pharmaceutical compositions and methods for reducing duration, intensity, and/or bothersomeness of common colds in humans and for reducing severity or duration of common cold symptoms such as nasal congestion, runny nose, watery eyes, dry/scratchy throat and sneezing in humans exhibiting such symptoms. The compositions herein comprise extracts of at least one of *Luffa Operculata* (*L. operculata*), *S. officinale* (*V. sabadilla*), and *Galphimia Glauca* (*G. glauca*) in a pharmaceutically acceptable carrier, and in various embodiments, comprise a mixture of all three *Luffa Operculata* (*L. operculata*) 10% extract MT, *S. officinale* (*V. sabadilla*) 3× extract, and *Galphimia Glauca* (*G. glauca*) 10% extract MT in a pharmaceutically acceptable carrier.

10 Claims, No Drawings

US 9,034,401 B1

PHARMACEUTICAL COMPOSITIONS COMPRISING PLANT EXTRACTS AND METHODS FOR REDUCING DURATION OF A COMMON COLD USING SAME

CROSS REFERENCE TO RELATED APPLICATIONS

This application claims priority to U.S. Provisional Patent Application Ser. No. 61/930,881 filed Jan. 23, 2014, which is incorporated herein by reference in its entirety.

FIELD OF THE INVENTION

The present disclosure relates generally to pharmaceutical compositions and methods of use thereof and in particular to nasal compositions comprising plant extracts and methods for reducing duration of a common cold in a human in need of treatment.

BACKGROUND OF THE INVENTION

The common cold is one of the most widespread viral diseases infecting mankind. It is universal and frequently contracted, infecting children and adults throughout their lives, and is one of the most common causes of doctor visits and absenteeism from school and work. The common cold is responsible for more widespread economic loss than perhaps most other medical conditions as measured by direct costs of $17 billion per year and indirect costs of $22.5 billion per year in the U.S. alone, (see A. Fendrick, et al., "The Economic Burden of Non-Influenza-Related Viral Respiratory Tract Infection in the United States," Arch. Intern. Med., 163(4), 487-494, 2003).

Currently there is no universally accepted, proven medical intervention that is widely available for treatment of the common cold. Most consumers use over-the-counter medications that reduce the inflammation associated with viral infections, in order to reduce the severity of their symptoms. These over-the-counter medications include analgesics, decongestants, mucolytics, and antihistamines, all of which reduce specific mediators of inflammation associated with colds symptoms. A product that is effective in the treatment of the common cold could markedly reduce the negative impact and economic losses otherwise incurred. A greater clinical benefit may be possible by interrupting the viral infection at more proximate points in the infection thereby mitigating the process and avoiding its evolution.

Rhinovirus infection is the most common cause of the common cold, (see R. Dolin, "Common Viral Respiratory Infections and Severe Acute Repiratory Syndrome (SARS)" in A. e. Fauci, *Harrison's Principles of Internal Medicine*, pp. 1120-1126, New York: McGraw Hill, 2008). The virus is typically introduced into the nasal passage where it quickly infects cells in the nasal mucosa, reproduces, then spreads to other epithelial cells through ciliary transport of new virions shed into the lumen. This process of viral replication and spread takes place within the first 8-24 hours, at which point symptoms of the colds illness begin to manifest, (see M. Terajima, "Rhinovirus Infection of Primary Cultures of Human Tracheal Epithelium: Role of ICAM-1 and IL-1β," *Am J Physiol—Lung Physiol.* 273 (4), L749-L759, 1997). Therefore, it is important to clinically intervene in the colds illness within the first 8-24 hours following infection.

Most researchers believe that intervening very early in the course of viral illness with compounds that interfere with viral replication, virus spread and infection provide the best chance of reducing its overall symptom burden. Few drugs have proven to work in relieving the common cold by interfering with the process of viral infection.

Therefore, new products usable during the manifestation of the colds illness are needed. For example, new pharmaceutical compositions usable for early intervention and reduction of duration of common colds are desirable.

SUMMARY OF THE INVENTION

Various embodiments of the present disclosure provide compositions and methods for reducing duration of common colds in humans and for reducing severity or duration of common cold symptoms such as nasal congestion, runny nose, watery eyes, dry/scratchy throat and sneezing.

In various embodiments, compositions that reduce duration of a common cold in a human expressing symptoms characteristic of the common cold, and that reduce severity or duration of common cold symptoms such as nasal congestion, runny nose, watery eyes, dry/scratchy throat and sneezing, comprise an extract of *Luffa Operculata* (*L. operculata*), *S. officinale* (*V. sabadilla*), and/or *Galphimia Glauca* (*G. glauca*) in a pharmaceutically acceptable carrier. In various embodiments, such compositions further comprise at least one drug active.

In various embodiments, compositions that reduce duration of a common cold in a human expressing symptoms characteristic of the common cold, and that reduce severity or duration of common cold symptoms such as nasal congestion, runny nose, watery eyes, dry/scratchy throat and sneezing, comprise extracts of *Luffa Operculata* (*L. operculata*), *S. officinale* (*V. sabadilla*), and *Galphimia Glauca* (*G. glauca*) in a pharmaceutically acceptable carrier. In various embodiments, such compositions further comprise at least one drug active.

In various embodiments, compositions useful for reducing duration of a common cold in a human expressing symptoms characteristic of the common cold, and for reducing severity or duration of common cold symptoms such as nasal congestion, runny nose, watery eyes, dry/scratchy throat and sneezing, are formulated into physical forms amenable to administration to the nasal mucosa of the subject in need of treatment. In various embodiments, administration of such compositions comprises applying a therapeutically effective amount of the composition into one or both nostrils of the human in need of treatment.

In various embodiments, compositions in accordance with the present disclosure, useful for reducing duration of common colds in humans and for reducing severity or duration of common cold symptoms such as nasal congestion, runny nose, watery eyes, dry/scratchy throat and sneezing, comprise: (a) at least one or any combination of *L. operculata* 10 wt. % extract (MT) at of about 0.001 wt. % to about 0.1 wt. %; *S. officinale* 3× extract at about 0.001 wt. % to about 0.1 wt. %; and *G. glauca* 10 wt. % extract (MT) at about 0.001 wt. % to about 0.1 wt. %; and (b) a pharmaceutically acceptable carrier.

In various embodiments, compositions in accordance with the present disclosure, useful for reducing duration of common colds in humans and for reducing severity or duration of common cold symptoms such as nasal congestion, runny nose, watery eyes, dry/scratchy throat and sneezing, comprise: (a) at least one or any combination of: *L. operculata* 10 wt. % extract (MT) at of about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) a surfactant at about 0.001 wt. % to about 10 wt. %; (d) an organic acid at about 0.01 wt. % to about 10 wt. %; (e) at least one of a carbonate, sulfate, and phosphate totaling about 0.01 wt. % to about 10 wt. %; (f) at least one inhalant at about 0.001 wt. % to about 1 wt. %; (g) optionally at least one amino acid at about 0.01 wt. % to about 10 wt. %; (h) optionally at least one salt at about 0.01 wt. % to about 1 wt. %; (i) optionally at least one fragrance at about 0.001 wt. % to about 1 wt. %; (j) optionally at least one sweetener at about 0.001 wt. % to about 1 wt. %; (k) optionally at least one of a preservative, ultraviolet inhibitor and antioxidant at about 0.001 wt. % to about 1 wt. %; (l) optionally a non-aqueous solvent or vehicle at about 0.001 wt. % to about 99 wt. %; and (m) remainder water, wherein each wt. % is based on the total weight of the composition.

In various embodiments, a method for reducing duration of a common cold comprises applying daily to the nasal passageways of a human in need of treatment a therapeutically effective amount of a composition comprising extracts of *L. operculata, S. officinale* and *G. glauca* in a pharmaceutically acceptable carrier. In various embodiments, the pharmaceutically acceptable carrier is predominately water. In various embodiments, the composition further comprises any combination of thickener, surfactant, acid, alkaline material, inhalant, amino acid, salt, drug active, fragrance, sweetener, and/or preservative.

In various embodiments, a method for reducing the severity or duration of common cold symptoms in humans, which includes reducing severity or duration of any one of nasal congestion, runny nose, watery eyes, dry/scratchy throat and sneezing, comprises nasal administration of a therapeutically effective amount of a pharmaceutical composition comprising extracts of *L. operculata, S. officinale* and *G. glauca* in a pharmaceutically acceptable carrier. In various embodiments, the pharmaceutically acceptable carrier is predominately water. In various embodiments, the composition further comprises any combination of thickener, surfactant, acid, alkaline material, inhalant, amino acid, salt, drug active, fragrance, sweetener, and/or preservative.

In various embodiments, a method for reducing the intensity or bothersomeness of a common cold comprises nasal administration of a therapeutically effective amount of a pharmaceutical composition comprising extracts of *L. operculata, S. officinale* and *G. glauca* in a pharmaceutically acceptable carrier. In various embodiments, the pharmaceutically acceptable carrier is predominately water. In various embodiments, the composition further comprises any combination of thickener, surfactant, acid, alkaline material, inhalant, amino acid, salt, drug active, fragrance, sweetener, and/or preservative.

In various embodiments, a method for reducing duration of a common cold in a human comprises nasal administration of a therapeutically effective amount of a pharmaceutical composition consisting essentially of: (a) from about 0.001 wt. % to about 0.5 wt. % of a mixture of *L. operculata* 10 wt. % extract (MT), *S. officinale* 3× extract and *G. glauca* 10 wt. % extract (MT); (b) from about 0.5 wt. % to about 1.5 wt. % of a cellulosic thickener; (c) from about 0.01 wt. % to about 1 wt. % of a surfactant; (d) from about 0.1 wt. % to about 1 wt. % of an organic acid; (e) from about 0.1 to about 2 wt. % of a mixture of sodium monobasic and sodium dibasic phosphate salts; (f) from about 0.1 wt. % to about 1 wt. % of a mixture of menthol, eucalyptol and eugenol; (g) from about 0.05 wt. % to about 0.5 wt. % of an amino acid; (h) from about 0.1 wt. % to about 1 wt. % sodium chloride; and (i) from about 90 wt. % to about 99 wt. % water, wherein each wt. % is based on the total weight of the composition.

In various embodiments, a method for reducing the severity or duration of common cold symptoms in humans, which includes reducing severity or duration of any one of nasal congestion, runny nose, watery eyes, dry/scratchy throat and sneezing, comprises nasal administration of a therapeutically effective amount of a pharmaceutical composition consisting essentially of: (a) from about 0.001 wt. % to about 0.5 wt. % of a mixture of *L. operculata* 10 wt. % extract (MT), *S. officinale* 3× extract and *G. glauca* 10 wt. % extract (MT); (b) from about 0.5 wt. % to about 1.5 wt. % of a cellulosic thickener; (c) from about 0.01 wt. % to about 1 wt. % of a surfactant; (d) from about 0.1 wt. % to about 1 wt. % of an organic acid; (e) from about 0.1 to about 2 wt. % of a mixture of sodium monobasic and sodium dibasic phosphate salts; (f) from about 0.1 wt. % to about 1 wt. % of a mixture of menthol, eucalyptol and eugenol; (g) from about 0.05 wt. % to about 0.5 wt. % of an amino acid; (h) from about 0.1 wt. % to about 1 wt. % sodium chloride; and (i) from about 90 wt. % to about 99 wt. % water, wherein each wt. % is based on the total weight of the composition.

In various embodiments, a method for reducing intensity or bothersomeness of a common cold in a human comprises nasal administration of a therapeutically effective amount of a pharmaceutical composition consisting essentially of: (a) from about 0.001 wt. % to about 0.5 wt. % of a mixture of *L. operculata* 10 wt. % extract (MT), *S. officinale* 3× extract and *G. glauca* 10 wt. % extract (MT); (b) from about 0.5 wt. % to about 1.5 wt. % of a cellulosic thickener; (c) from about 0.01 wt. % to about 1 wt. % of a surfactant; (d) from about 0.1 wt. % to about 1 wt. % of an organic acid; (e) from about 0.1 to about 2 wt. % of a mixture of sodium monobasic and sodium dibasic phosphate salts; (f) from about 0.1 wt. % to about 1 wt. % of a mixture of menthol, eucalyptol and eugenol; (g) from about 0.05 wt. % to about 0.5 wt. % of an amino acid; (h) from about 0.1 wt. % to about 1 wt. % sodium chloride; and (i) from about 90 wt. % to about 99 wt. % water, wherein each wt. % is based on the total weight of the composition.

DETAILED DESCRIPTION OF THE INVENTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

As described in more detail herein, various embodiments of the present disclosure generally comprise a composition for treatment of the common cold, wherein the composition comprises: an extract of *Luffa Operculata* (*L. operculata*), *Schoenocaulon officinale* (*S. officinale*), and/or *Galphimia Glauca* (*G. glauca*); and a pharmaceutically acceptable carrier. Various embodiments of the present disclosure also comprise methods for reducing duration of common colds in humans and for reducing the severity or duration of common cold symptoms in humans such as nasal congestion, runny nose, watery eyes, dry/scratchy throat and sneezing, by administration of a composition comprising: (a) an extract of *Luffa Operculata* (*L. operculata*), *Schoenocaulon officinale* (*S. officinale*), and/or *Galphimia Glauca* (*G. glauca*); and (b) a pharmaceutically acceptable carrier, to the nasal passageways of a human exhibiting symptoms of the common cold.

The Plant Extracts

In various embodiments, the compositions in accordance to the present disclosure comprise an extract of *Luffa Operculata* (*L. operculata*), *Schoenocaulon officinale* (*S. officinale*), and/or *Galphimia Glauca* (*G. glauca*). In various embodiments, the compositions comprise only one of *Luffa Operculata* (*L. operculata*), *Schoenocaulon officinale* (*S. officinale*), and *Galphimia Glauca* (*G. glauca*) extract. In various embodiments, the compositions comprise combinations of any two of *Luffa Operculata* (*L. operculata*), *Schoenocaulon officinale* (*S. officinale*), and *Galphimia Glauca* (*G. glauca*) extracts. In various other embodiments, the compositions comprise *Luffa Operculata* (*L. operculata*), *Schoenocaulon officinale* (*S. officinale*) and *Galphimia Glauca* (*G. glauca*) extracts. Each of these plants and their extracts are discussed below.

The particular extracts and dilutions therefrom are not intended to be limiting. As used herein, the term "extract" includes the terms "tincture" and "infusion." In some recitations herein the terms are used interchangeably. These terms herein refer generally to a liquid composition containing biological materials (natural products) obtained by exposing plant parts to various solvents, such as water and/or alcohol or other suitable solvents, under various conditions (e.g. heating or ambient), for various lengths of time (seconds, minutes, days, weeks, months, etc.). Extracts may be filtered to remove solids, decanted, diluted, or used as is. It some instances, the biological materials in an extract may be identified and known (e.g. particular alkaloids, flavonoids, etc.), but it should be appreciated that for many plant extracts, the biologic materials present in the extract remain unidentifiable and uncharacterized.

*L. operculata* Extract (MT)

*Luffa operculata* (*L. operculata*, or the sponge cucumber) is a particular species of *Luffa*, from the family Cucurbitaceae. *L. operculata* is a smaller version of the more familiar *L. cylindrica*, the fruit of which is best known as the "loofah" sponge. The fruit from *L. operculata* is dried into smaller size sponges than the sponges available from fruits of *L. cylindrica*.

*L. operculata* has been found to contain ceramides, a rare triterpenoid, and various steroids in the bark of the fruit and in the stems of the plant. The ceramides were shown to have high acetylcholine esterase inhibitory effects. See C. Feitosa, R. Silva, R. Braz-Filho, J. Menezes, S. Siqueira and F. Monte, "Characterization of Chemical Constituents of *Luffa operculata* (Cucurbitaceae)," *American Journal of Analytical Chemistry*, Vol. 2 No. 8, 2011, pp. 989-995. In a separate study, an aqueous extract of *L. operculata* was tested in mice for toxicity, alteration of neuromuscular coordination, analgesic effects, blood pressure and pulse changes, electrocardiographic and respiratory patterns, and anti-inflammatory activity, amongst others. The aqueous extract was also tested in guinea pigs for protective effects against histamine-induced bronchospasm. The extract was found to be inactive in all tests except for the analgesic studies in mice. See Ronald Champnew, Noel M. Ferguson and Gary G. Ferguson, "Selected Pharmacological Studies of *Luffa Operculata*," *Journal of Pharmaceutical Sciences*, Vol. 63, Issue 6, 1974 pp 942-943.

*L. operculata*, ext. has been assigned CAS No. 90063-68-3. The extract for use herein, (also denoted as the "mother tincture" or "MT"), is prepared from *L. operculata* fruit material (peel, fibrous pulp, and/or seeds) and alcohol (ethanol), whereby 1 part by weight botanical substance is combined with 9 parts by weight alcohol. Thus for example, a mixture of 100 grams *L. operculata* fruit material and 900 grams ethanol will produce approximately a 1,000 gram (1 Kg) batch of *L. operculata* 10 wt. % extract (MT).

*L. operculata* 10 wt. % extract (MT), prepared as described herein above, may be incorporated in the compositions of the present disclosure at levels of about 0.001 wt. % to about 0.1 wt. %, based on the total weight of the composition.

*S. officinale* 3× Extract

*Schoenocaulon officinale* (formerly *Veratrum sabadilla*, *Sabadilla Veratrum sabadilla*, or *Veratrum officinale*) is a plant from the family Liliaceae (lily). The alkaloids veracevine, cevadine, veratridine, cevacine and 3-O-vanilloylceracevine are collectively known as "veratrine" or the "Sabadilla Alkaloids," and are obtained at about 2-4% from the crushed seeds of the plant. Veratrine primarily comprises a 2:1 mixture of cevadine ($C_{32}H_{49}NO_9$; CAS No. 62-59-9) and veratridine ($C_{36}H_{51}NO_{11}$; CAS No. 71-62-5), with minor amounts of the other materials. See "Sabadilla Alkaloids" in Hayes' *Handbook of Pesticide Toxicology*, Vol. 1, Chapter 3, pp 142-145, W. J. Hayes, editor, Academic publishers (2010). The Sabadilla Alkaloids are known for their use as insecticides, however have not been disclosed as having any antiviral efficacy, (see M. Ikawa, R. J. Dicke, T. C. Allen and K. P. Link, "The Principal Alkaloids of Sabadilla Seed and their Toxicity to *Musca Domestical* L.," *J. Biol. Chem.*, 1945, 159:517-524). For example, a powder prepared from the dried seeds of *Schoenocaulon Officinale* has been used to expel parasitic worms and to kill mites in hair. Veratrine is used against thrips in citrus and avocado farming. Being weak bases, the Sabadilla Alkaloids are soluble at acidic pH.

*S. officinale*, 3× extract, as used herein, is a successive dilution of the mother tincture obtained directly from the plant material and alcohol. The 3× extract for use herein begins with *S. officinale* seeds and alcohol (ethanol), whereby 1 part by weight botanical substance is combined with 9 parts by weight alcohol to produce the MT. 1 mL MT diluted with 9 mL alcohol produces the 2× attenuation. Lastly, 1 mL of the 2× attenuation diluted with 9 mL alcohol produces the 3× attenuation, denoted "*S. officinale* 3× extract."

*S. officinale* 3× extract, prepared as described herein above, may be incorporated in the compositions of the present disclosure at levels of about 0.001 wt. % to about 0.1 wt. %, based on the total weight of the composition.

*G. glauca* Extract (MT)

*Galphimia glauca* (*G. glauca*) is one of many species of small, tropical evergreen shrubs of the genus Galphimia and family Malpighiaceae. *G. glauca* grows as a shrub, about 1.8 meters in height, having leaves measuring about 6×3 cm. The flowers are up to 2.3 cm wide and often spread out flat. Extracts of the leaves and flowers (blossoms or open flowers) have found some medicinal uses. For example, a tea infusion of Galphimia has been used to treat diarrhea, dysentery and gastroenteritis.

*G. glauca* extract has been assigned CAS No. 90045-22-0. The extract for use herein, (also denoted as the "mother tincture" or "MT"), is prepared from *G. glauca* leaves and blossoms (flower material) and alcohol (ethanol), whereby 1 part by weight botanical substance is combined with 9 parts by weight alcohol. Thus for example, a mixture of 100 grams *G. glauca* leaf and flower material and 900 grams ethanol will produce approximately a 1,000 gram (1 Kg) batch of *G. glauca* 10 wt. % extract (MT).

*G. glauca* 10 wt. % extract (MT), prepared as described herein above, may be incorporated in the compositions of the present disclosure at levels of about 0.001 wt. % to about 0.1 wt. %, based on the total weight of the composition.

In various embodiments, compositions of the present disclosure may comprise any one or combination of *L. opercu-*

*lata* 10 wt. % extract (MT), *S. officinale* 3× extract, and/or *G. glauca* 10 wt. % extract (MT), at a total level of about 0.001 wt. % to about 0.5 wt. %, based on the total weight of the composition.

In various embodiments, compositions of the present disclosure comprise *L. operculata* 10 wt. % extract (MT), *S. officinale* 3× extract, and *G. glauca* 10 wt. % extract (MT) at a total level of about 0.01 wt. % to about 0.5 wt. %, based on the total weight of the composition.

The Pharmaceutically Acceptable Carrier

In various embodiments, a pharmaceutical acceptable carrier in accordance with the present disclosure may comprise any one or combinations of thickeners, surface modifying agents (surfactants), pH adjusters, pH buffers, amino acids, inhalants, fragrances, salts, drug actives, preservatives, uv inhibitors, antioxidants, flavorings, sweeteners, water, non-aqueous solvents, petroleum-based vehicles, and other adjuvants, to achieve a particular dosage form, final concentration of plant extract(s) or other actives, method of administration, therapeutic efficacy, cost, physical stability, consumer acceptability, marketing advantage, and/or any other technical or business goal.

Thickeners

Pharmaceutical compositions in accordance with various embodiments of the present disclosure may further comprise one or more thickeners. Such materials may be natural, synthetic or semisynthetic, and may be organic/polymeric or inorganic substances, or mixtures thereof. Polymers may include homo-polymers, random co-polymers and block co-polymers. Polymers may also include proteins such as albumin, or other natural polymers such as chitin or xanthan. Inorganic thickening agents may include, but are not limited to, such materials as clays and silica gel. A thickener used herein may be nonionic, anionic, cationic, or amphoteric, or an inorganic mineral or salt. A thickener may be incorporated as its salt (partial or full) having any counterion(s), (e.g. $Na^+$, $K^+$, $Cl^-$, etc.) as appropriate for particular ionizable groups therein.

Thickeners may be used to provide any one, or combination of, bulk, viscosity or rheology characteristics in the compositions. In various embodiments, one or more thickeners may be added to impart certain rheology characteristics to the present compositions, such as a desired shear, yield, deformation, plasticity, elasticity, viscoelasticity, pseudo-plasticity, or the like. In various embodiments, one or more thickeners, acting as bulking agent(s), may also be added to reach a particular bulk density target. In various embodiments, one or more thickeners may also be added to impart other physical characteristics such as a particular spray droplet size, dispensing dose size, cling and/or feel within the nasal passages or in the mouth.

Thickening agents include, but are not limited to, carboxymethyl cellulose, carboxyethyl cellulose, hydroxyethyl cellulose, hydrophobically modified hydroxyethyl cellulose, hydroxypropyl cellulose, hydroxypropyl methyl cellulose, methyl cellulose, ethyl cellulose, microcrystalline cellulose, nitrocellulose and other cellulosic thickeners, polyvinyl alcohol, polyvinylpyrrolidone, polyvinylmethacrylate, polyacrylates, acrylate co-polymers such as acrylic acid/vinyl pyrrolidone cross-polymer, carboxyvinyl polymers, polyvinylacetate, polyvinyl co-polymers, polyurethanes, various starches, modified starches, dextrin, xanthan and other gums, agar, alginic acid and alginates, pectin, gelatin and other hydrocolloids, gelling agents, casein, albumin, chitin, collagen, silica gel, fumed silica, magnesium aluminum silicates, clay, bentonite, hectorite, and combinations thereof.

One or more thickeners may be incorporated in the compositions of the present disclosure at levels of about 0.001 wt. % to about 10 wt. %, based on the total weight of the composition.

In various embodiments, the compositions of the present disclosure comprise a cellulosic thickener at a level of about 0.001 wt. % to about 10 wt. %, based on the total weight of the composition. In various embodiments, the compositions of the present disclosure comprise hydroxypropyl methyl cellulose (HPMC, hypromellose) at a level of about 0.001 wt. % to about 10 wt. %, based on the total weight of the composition.

Surfactants

Pharmaceutical compositions in accordance with various embodiments of the present disclosure may further comprise one or more surfactants. As used herein, the term "surfactant" is intended to include emulsifiers and solubilizers because some surfactants function as emulsifiers or solubilizers depending on their chemical structure and the co-ingredients in a particular composition. Surfactants for use herein may be anionic, nonionic, amphoteric or cationic.

Exemplary anionic surfactants include, but are not limited to, fatty acids, alkyl sulfates, alkyl ether sulfates, alkyl aryl sulfonates, alkyl succinates, alkyl sulfosuccinates, N-alkoyl sarcosinates, alkyl phosphates, alkyl ether phosphates, alkyl ether carboxylates, alkylamino acids, alkyl peptides, alkoyl taurates, acyl and alkyl glutamates, alkyl isethionates, α-olefin sulfonates, and combinations thereof.

Exemplary nonionic surfactants include, but are not limited to, aliphatic primary or secondary linear or branched chain fatty alcohols or phenols, fatty acid esters, mono-, di-, and tri-fatty acid glycerides, alkyl alkoxylates, alkyl phenol alkoxylates, block alkylene oxide condensates of alkyl phenols, alkylene oxide condensates of alkanols, ethylene oxide/propylene oxide (EO/PO) block copolymers, amine oxides, phosphine oxides, mono- or di-alkyl alkanolamides, alkyl polysaccharides, sorbitan fatty acid esters, polyoxyethylene sorbitan fatty acid esters, polyoxyethylene sorbitol esters, polyoxyethylene esters, polyoxyethylene alcohols, mono- and diethanolamides, polyglycosides, polyglucosides, diglucoside, alkyl polyglucoside, polysorbates, alkoxylated fatty alcohols, alkoxylated fatty acid glycerides, and mixtures thereof.

Exemplary amphoteric surfactants include, but are not limited to, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, acyl glutamates, and mixtures thereof.

Exemplary cationic surfactants include, but are not limited to, quaternary alkyl amines, alkyl imidazolines, quaternary ethoxylated amines, quaternized amides, and combinations thereof. Some quaternary compounds, such as benzalkonium chloride, can function as antimicrobial agents (e.g. preservatives, discussed herein below), although they are cationic surfactants structurally.

One or more surfactants may be incorporated in the compositions of the present disclosure at levels of about 0.001 wt. % to about 10 wt. %, based on the total weight of the composition.

In various embodiments, the compositions of the present disclosure comprise the nonionic surfactant, polyethoxylated sorbitan laurate and/or oleate ester at a level of about 0.01 to about 1.0 wt. %, based on the total weight of the composition. In various embodiments, the compositions of the present disclosure comprise polyoxyethylene (20) sorbitan monooleate (polysorbate 80, or TWEEN® 80) at a level of about 0.01 to about 1.0 wt. %, based on the total weight of the composition.

pH Adjusters and pH Buffers

Pharmaceutical compositions in accordance with various embodiments of the present disclosure may further comprise one or more acidifying agents or alkaline agents as necessary to neutralize various co-ingredients, form salts of various co-ingredients, and/or achieve a particular pH target for the composition. In various embodiments of the present disclosure, the compositions are acidic, having a pH of less than about 7. In various embodiments, the pH of the composition is from about 2 to about 6. Combinations of various acidifying agents and alkaline agents may be used to create buffering systems to stabilize the desired pH of the composition. Buffers may be mixed buffers, meaning that the alkaline agent is not necessarily the conjugate base of the acidifying agent.

Exemplary acidifying agents for use in the present compositions include, but are not limited to, organic acids of any molecular weight and mineral acids (inorganic acids), and mixtures thereof. Organic acids may include mono-carboxylic acids, di-carboxylic acids, or tri-carboxylic acids, and may be saturated or may have any degree of unsaturation. For example, organic acids for use in various embodiments of the composition in accordance to the present disclosure may include, but are not limited to, formic acid, carbonic acid, acetic acid, lactic acid, oxalic acid, propionic acid, valeric acid, enanthic acid, pelargonic acid, butyric acid, lauric acid, docosahexaenoic acid, eicosapentaenoic acid, pyruvic acid, acetoacetic acid, benzoic acid, salicylic acid, aldaric acid, fumaric acid, glutaconic acid, traumatic acid, muconic acid, malonic acid, malic acid, succinic acid, glutaric acid, adipic acid, pimelic acid, suberic acid, azelaic acid, abietic acid, pimaric acid, sebacic acid, phthalic acid, isophthalic acid, terephthalic acid, maleic acid, citric acid, and combinations thereof. For example, mineral acids for use in various embodiments of the composition in accordance to the present disclosure may include, but are not limited to hydrochloric acid, phosphoric acid, sulfuric acid, nitric acid, and combinations thereof.

One or more organic and/or mineral acids may be incorporated in the compositions of the present disclosure at levels of about 0.01 wt. % to about 10 wt. %, based on the total weight of the composition.

In various embodiments, the compositions of the present disclosure comprise at least one mono-carboxylic acid at a level of about 0.01 to about 10 wt. %, based on the total weight of the composition. In various embodiments, the compositions of the present disclosure comprise at least one di-carboxylic acid at a level of about 0.01 to about 10 wt. %, based on the total weight of the composition. In various embodiments, the compositions of the present disclosure comprise at least one tri-carboxylic acid at a level of about 0.01 to about 10 wt. %, based on the total weight of the composition. In various embodiments, the compositions of the present disclosure comprise any single one, or combination, of mono-, di-, and tri-carboxylic acids. In various embodiments, the compositions of the present disclosure comprise at least one of malonic, maleic, succinic, glutaric and adipic acids, at a total level of about 0.01 to about 10 wt. %, based on the total weight of the composition. In various embodiments, the compositions of the present disclosure comprise succinic acid at a level of about 0.01 to about 1 wt. %, based on the total weight of the composition.

Exemplary alkaline materials include any organic amines, $NH_3$, alkali metal or alkaline earth hydroxide, any conjugate bases of any organic acids (e.g. R-000"), and any of the salts of carbonic acid, phosphoric acid, nitric acid and sulfuric acid, and any mixtures thereof. For example, alkaline materials for use in various embodiments of the composition in accordance to the present disclosure may include, but are not limited to, NaOH, KOH, $NH_3$, sodium acetate, sodium succinate, disodium succinate, monosodium citrate, disodium citrate, trisodium citrate, $NaH_2PO_4$, $Na_2HPO_4$, $Na_3PO_4$, $KH_2PO_4$, $K_2HPO_4$, $K_3PO_4$, $NaHSO_4$, $Na_2SO_4$, $KHSO_4$, $K_2SO_4$, $NaHCO_3$, $Na_2CO_3$, $KHCO_3$, $K_2CO_3$, $NaH_3P_2O_7$, $Na_2H_2P_2O_7$, $Na_3HP_2O_7$, $Na_4P_2O_7$, $KH_3P_2O_7$, $K_2H_2P_2O_7$, $K_3HP_2O_7$, $K_4P_2O_7$, and mixtures thereof. Any of these chemical species may exist as various hydrates when purchased as raw materials for use in the present compositions.

One or more alkaline agents may be incorporated in the compositions of the present disclosure at levels of about 0.01 wt. % to about 10 wt. %, based on the total weight of the composition.

In various embodiments, the compositions of the present disclosure comprise at least one salt of carbonic acid or phosphoric acid at a level of about 0.01 to about 10 wt. %, based on the total weight of the composition. In various embodiments, the compositions of the present disclosure comprise at least one of sodium phosphate dibasic ($Na_2HPO_4$) and sodium phosphate monobasic ($NaH_2PO_4$) at a level of about 0.1 to about 5 wt. %, based on the total weight of the composition. In various embodiments, the compositions of the present disclosure comprise sodium phosphate dibasic ($Na_2HPO_4$) and sodium phosphate monobasic ($NaH_2PO_4$) at a total level of about 0.1 to about 5 wt. %, based on the total weight of the composition.

In various embodiments, the compositions of the present disclosure comprise sodium phosphate dibasic ($Na_2HPO_4$) and sodium phosphate monobasic ($NaH_2PO_4$), at a total level of about 0.1 to about 5 wt. %, based on the total weight of the composition, and at least one of malonic, maleic, succinic, glutaric and adipic acids, at a level of about 0.01 to about 10 wt. %, based on the total weight of the composition, to form a final pH of about 2-6 and a mixed buffer system. In various embodiments, the compositions of the present disclosure comprise sodium phosphate dibasic ($Na_2HPO_4$) and sodium phosphate monobasic ($NaH_2PO_4$), at a total level of about 0.1 to about 5 wt. %, based on the total weight of the composition, and succinic acid at a level of about 0.01 to about 10 wt. %, based on the total weight of the composition, to form a final pH of about 4 to about 5, and a mixed buffer system.

Amino Acids

Pharmaceutical compositions in accordance with various embodiments of the present disclosure may further comprise one or more natural, synthetic, semi-synthetic, common, uncommon, known, or unknown amino acids, in any combination, wherein the one or more amino acids comprise any juxtaposition of the —$NH_2$ and —$CO_2H$ substituents, (e.g., α-, β-, γ-, δ-, etc.).

Table 1 lists common α-amino acids that, in various embodiments, find use in the compositions of the present disclosure. A number of these amino acids are known to possess antimicrobial efficacy. For example, L-lysine is a known antiviral agent and combinations of glycine with other amino acids have been shown to promote wound healing. Amino acids, in combination with the acidifying and alkaline agents above, may provide pH adjusting and pH buffering functions.

TABLE 1

| Common α-Amino Acids | | |
|---|---|---|
| Amino Acid | Abbreviation | Formula (molecular weight) |
| Alanine | Ala | $C_3H_7NO_2$ (89.09) |
| Arginine | Arg | $C_6H_{14}N_4O_2$ (174.20) |

TABLE 1-continued

Common α-Amino Acids

| Amino Acid | Abbreviation | Formula (molecular weight) |
| --- | --- | --- |
| Asparagine | Asn | $C_4H_8N_2O_3$ (132.12) |
| Aspartic Acid | Asp | $C_4H_7NO_4$ (133.10) |
| Cysteine | Cys | $C_3H_7NO_2S$ (240.30) |
| Glutamic Acid | Glu | $C_5H_9NO_4$ (147.13) |
| Glutamine | Gln | $C_5H_{10}N_2O_3$ (146.15) |
| Glycine | Gly | $C_2H_5O_2$ (75.07) |
| Histidine | His | $C_6H_9N_3O_2$ (155.16) |
| Isoleucine | Ile | $C_6H_{13}NO_2$ (131.18) |
| Leucine | Leu | $C_6H_{13}NO_2$ (131.18) |
| Lysine | Lys | $C_6H_{14}N_2O_2$ (146.19) |
| Methionine | Met | $C_5H_{11}NO_2S$ (149.21) |
| Phenylalanine | Phe | $C_9H_{11}NO_2$ (165.19) |
| Proline | Pro | $C_5H_9NO_2$ (115.13) |
| Serine | Ser | $C_3H_7NO_3$ (105.19) |
| Threonine | Thr | $C_4H_9NO_3$ (119.12) |
| Tryptophan | Trp | $C_{11}H_{10}N_2O_2$ (204.23) |
| Tyrosine | Tyr | $C_9H_{11}NO_3$ (181.19) |
| Valine | Val | $C_5H_{11}NO_2$ (117.15) |

One or more amino acids may be incorporated in the compositions of the present disclosure at levels of about 0.01 wt. % to about 10 wt. %, based on the total weight of the composition.

In various embodiments, from about 0.01 wt. % to about 10 wt. % of at least one of glycine and L-lysine is used, based on the total weight of the composition. In various embodiments, the compositions of the present disclosure comprise from about 0.01 wt. % to about 10 wt. % glycine, based on the total weight of the composition.

Inhalants

The term "inhalant," as used herein, refers to organic substances that have a notable "aromatic" or otherwise "strong" odor, sometimes associated with vaporizers and other home remedies to relieve sinus congestion. "Aromatic" is not strictly used herein to limit the inhalants to aromatic compounds in the organic chemistry sense (i.e., those compounds having aromatic unsaturation), but rather to include all molecules having a low vapor pressure and a smell that may be described, for example, as "medicinal." Inhalants, as classified herein, overlap to some degree with fragrances. Inhalants may include aromatic compounds (i.e. compounds having an unsaturated ring), terpene or terpenoid compounds, small molecular weight volatile organic compounds, amongst others, and combinations thereof. Lists of useful inhalants for the compositions of the present disclosure may appear to be chemically unrelated. Inhalants finding use in the present disclosure may contain one or more chiral centers, in which case the particular inhalant(s) chosen for use may comprise a single enantiomer, a racemate, or any combination of diastereoisomers depending on the number of chiral centers and their individual chirality. Further, various oils may be used as well as inhalants when they contain volatile substances. Non-limiting examples include: Japanese peppermint oil, known to contain substantial amounts of menthol; orange oil, known to contain substantial amounts of D-limonene; and clove oil, known to contain a substantial amount of eugenol.

Exemplary inhalants for use in the present compositions include, but are not limited to, anethole, menthol, eucalyptol, borneol, borneol acetate, camphor, 1,8-cineole, cinnamaldehyde, benzaldeyhde, citral, thuj one, eugenol, limonene, geraniol, citronellol, citronellal, pinene, linalool, thymol, carvone, caryphyllene, linalyl acetate, methyl salicylate, and mixtures thereof.

One or more inhalants may be incorporated in the compositions of the present disclosure at levels of about 0.001 wt. % to about 1 wt. %, based on the total weight of the composition.

In various embodiments, the compositions of the present disclosure comprise at least one inhalant selected from the group consisting of eucalyptol, eugenol, menthol, camphor, and mixtures thereof, at a total level of from about 0.001 wt. % to about 1 wt. %, based on the total weight of the composition. In various embodiments, the compositions of the present disclosure comprise at least one of eucalyptol, eugenol, and menthol at a total level of about 0.001 wt. % to about 1 wt. %, based on the total weight of the composition. In various embodiments, the compositions of the present disclosure comprise eucalyptol, eugenol and menthol at a total level of about 0.001 wt. % to about 1 wt. %, based on the total weight of the composition.

Fragrances

In various embodiments, the compositions of the present disclosure may comprise at least one fragrance. As mentioned, fragrances overlap with odoriferous compounds mentioned above that, for purposes herein, were categorized as inhalants. Fragrances may comprise essential oils, or may be synthetic or semi-synthetic. Some fragrances, for example some essential oils and phenolic solvents, have bacteriostatic and/or other preservative effects, and could equally be categorized and used as "preservatives" within the present disclosure.

Exemplary fragrances for use in the compositions of the present disclosure include, but are not limited to 3,3,5-trimethylcyclohexanol, methoxycyclohexanol, benzyl alcohol, anise alcohol, cinnamyl alcohol, O-phenyl ethyl alcohol (2-phenylethanol), cis-3-hexenol, musk xylol, isoeugenol, methyl eugenol, α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, hydroxycitronellal, benzaldehyde, methyl nonyl acetaldehyde, dodecanol, α-hexylcinnamic aldehyde, undecenal, heliotropin, vanillin, ethyl vanillin, methyl amyl ketone, methyl O-naphthyl ketone, methyl nonyl ketone, musk ketone, diacetyl, acetyl propionyl, acetyl butyryl, acetophenone, p-methyl acetophenone, ionone, methyl ionone, amyl butyrolactone, diphenyl oxide, methyl phenyl glycidate, γ-nonyl lactone, coumarin, cineole, ethyl methyl phenyl glicydate, methyl formate, isopropyl formate, linalyl formate, ethyl acetate, octyl acetate, methyl acetate, benzyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, β-phenylethyl acetate, trichloromethylphenyl carbinyl acetate, terpinyl acetate, vetiveryl acetate, and mixtures thereof.

In various embodiments, the compositions of the present disclosure comprise at least one fragrance at levels of about 0.001 wt. % to about 1 wt. %, based on the total weight of the composition. In various embodiments, the compositions of the present disclosure comprise 2-phenylethanol at a level of about 0.001 wt. % to about 1 wt. %, based on the total weight of the composition.

Preservatives, uv Inhibitors and Antioxidants

In various embodiments, the compositions of the present disclosure may comprise at least one of a preservative, uv Inhibitor, and antioxidant. Preservatives, such as quaternary ammonium compounds, may be antimicrobial in function, for example, exhibiting protection against mold and bacteria growth in finished products. Ultraviolet (uv) inhibitors protect the composition from damage by light. Antioxidants, such as BHT (butylated hydroxytoluene), can be used to protect compositions from oxidation.

In various embodiments, the compositions of the present disclosure comprise at least one of a preservative, ultraviolet inhibitor and antioxidant, at a level of about 0.001 wt. % to about 1 wt. %, based on the total weight of the composition.

In various embodiments, the compositions of the present disclosure comprise at least one of an N-alkyl-N-benzyl-N, N-dimethyl quaternary ammonium salt (an ADBAC quat), a uv inhibitor and BHT, each at levels of about 0.001 wt. % to about 1 wt. %, based on the total weight of the composition. In various embodiments, the compositions of the present disclosure comprise benzalkonium chloride at a level of about 0.001 wt. % to about 1 wt. %, based on the total weight of the composition. Benzalkonium chloride for use herein may be obtained as a 50% active solution.

Sweeteners

In various embodiments, the compositions of the present disclosure comprise a sweetener, such as, for example, any sugar (fructose, glucose, sucrose) or sugar alcohol (sucralose, and xylitol), potassium acesulfame, aspartame, neotame, saccharin, stevia, and mixtures thereof. In various embodiments, the compositions of the present disclosure comprise at least one sweetener at a level of about 0.001 wt. % to about 1 wt. %, based on the total weight of the composition.

Non-Aqueous Solvents/Vehicles

In various embodiments, the compositions of the present disclosure comprise a non-aqueous solvent, such as, for example, any alcohol or an oily or waxy vehicle (petrolatum, stearyl alcohol, lanolin, yellow wax, polyethylene glycol ointment, and the like). In various embodiments, the compositions of the present disclosure comprise ethyl alcohol (ethanol) at a level of about 0.001 wt. % to about 99 wt. %, based on the total weight of the composition. In various embodiments, the compositions of the present disclosure comprise an oily or waxy vehicle at a level of about 0.001 wt. % to about 99 wt. %, based on the total weight of the composition.

Salts

In various embodiments, the compositions of the present disclosure comprise a salt, such as, for example, sodium chloride and/or potassium chloride. In various embodiments, the compositions of the present disclosure comprise sodium chloride at a level of about 0.01 wt. % to about 1 wt. %, based on the total weight of the composition.

Drug Actives

In various embodiments, the compositions of the present disclosure comprise at least one drug active. The term "drug active," as used herein, refers to a drug having at least some antiviral and/or antibacterial activity when administered topically or systemically in/on a human. Such drugs may have been the subject of an FDA or foreign drug approval, presently in the market or marketed in the past, or may be entirely experimental, unknown, newly discovered, or as yet, undiscovered. Such drugs may be synthetic organic compounds or natural products, or derivatives thereof.

Exemplary drug actives for use in the compositions of the present disclosure include, but are not limited to, zanamivir (RELENZA®), oseltamivir (TAMIFLU®), abacavir (ZIAGEN®), adefovir, rimantadine, rimantadine hydrochloride, amantadine, ribavirin, synthetic sialic acid analogs in general, penicillins, benzylpenicillin, amoxycillin, ampicillin, cephalosporins, erythromycin, co-trimoxazole and other antibiotics, α- β- and γ-interferon, inosine pranobex, moroxydine hydrochloride, acyclovir and other antiviral agents in general, and mixtures thereof. A drug active may be used in the compositions of the present disclosure at a level of about 0.00001 wt. % to about 1 wt. %, depending on the nature of the drug active and the finished dosage form of the composition.

In various embodiments, compositions in accordance with the present disclosure comprise from about 0.1 wt. % to about 1 wt. % oseltamivir, based on the total weight of the composition. In various embodiments, compositions in accordance with the present disclosure comprise about 0.6 wt. % oseltamivir such that the finished composition has the same active oseltamivir level as TAMIFLU® 6 mg/mL suspension, (i.e. about 6 mg active drug per mL of composition).

Water

The compositions in accordance with the present disclosure may comprise a significantly large amount of water, for example, when the finished composition is in the form of a liquid. For example, water can make up most of the pharmaceutically acceptable carrier by weight. In other physical forms besides liquids, the compositions in accordance with the present invention may have much less water, such as in the case of an ointment or paste. The water used herein may be from any source and may have been subjected to any purification process prior to use. For example, the water may be distilled or reverse osmosis water.

In various embodiments, the compositions of the present disclosure comprise at least about 50 wt. % water, based on the total weight of the composition. In various embodiments, the compositions of the present disclosure comprise at least about 85 wt. % water, based on the total weight of the composition. In various embodiments, the compositions of the present disclosure comprise at least about 90 wt. % water, based on the total weight of the composition. In various embodiments, the compositions of the present disclosure comprise at least about 95 wt. % water, based on the total weight of the composition. In various embodiments, the compositions of the present disclosure comprise at least about 98 wt. % water, based on the total weight of the composition. In various embodiments, the compositions of the present disclosure comprise at least about 99 wt. % water, based on the total weight of the composition. In various embodiments, the compositions of the present disclosure comprise from about 90 wt. % to about 99 wt. % water, based on the total weight of the composition.

Dosage Form and General Methods of Treatment

Compositions formulated in accordance with the present disclosure may be expressed in any dosage form, such as, but not limited to, pills, tablets, capsules, lozenges, chewable tablets, gels, liquids, aerosols, pre-treated applicators, waxes, pastes, salves, ointments, injectables, amongst other forms. As such, water and non-aqueous solvent amounts may be adjusted accordingly (even to extremes) to accommodate formulation into these various dosage forms. "Pastes," as the term is used here, also incorporates highly viscous, non-aqueous petrolatum-based pharmaceutical compositions, such as those that are useful for application with a swab.

Methods of treatment in a human include, but are not limited to, topical, ocular, nasal, otic, and oral administration, ingestion, and injection of the compositions of the present disclosure. Methods of treatment in a human also extend to the use of compositions of the present disclosure in combination with any other pharmaceutical composition, be it registered, regulated, unregistered, unregulated, experimental, theoretical, now known or presently unknown, in accordance to any combination dosage regimen thereby, and wherein the combination pharmaceutical composition is in any physical dosage form.

Usage of various compositions in accordance to the present disclosure include (1) reducing duration and/or intensity or bothersomeness of a common cold in a human; and (2) reducing the severity, bothersomeness, and/or duration of cold symptoms including nasal congestion, runny nose, watery eyes, dry/scratchy throat and/or sneezing, in a human exhibiting such symptoms.

In various embodiments, the compositions of the present disclosure comprise nasal compositions having physical form amendable to application to the nasal passages and/or mucosa of a human in need of treatment. These forms include, but are not limited to, gels, treated swabs (e.g. swabs pre-wetted with a liquid, gel or paste), liquids, and pastes. In various embodiments, the compositions of the present disclosure are liquid, generally aqueous-based, nasal sprays that can be aerosolized through a non-aerosol sprayer, (e.g. a squeeze bottle having a pin-hole spray exit, or a finger-actuated non-aerosol sprayer), or through a pressurized aerosol system.

Liquid spray nasal compositions in accordance with the present disclosure may be administered into the nasal passages of a human in need of treatment by spraying approximately 50-250 µL of the liquid composition from any dispenser into one or both nostrils. Administration may be daily or may follow any other effective dosage schedule (every other day, bi-weekly, weekly, etc.). Administration of nasal compositions disclosed herein into the nostrils of the human in need of treatment may be once per day, twice per day, three times per day, four times per day, five times per day, six times per day, or as many times per day as required to reduce duration of a common cold in a human having a common cold and/or as needed to reduce the severity and/or duration of cold symptoms in a human exhibiting such symptoms as nasal congestion, runny nose, watery eyes, dry/scratching throat and/or sneezing. Similar dosing amounts and regimens are conceivable using pre-treated swabs, having liquid, gel or paste form on the swab.

For example, in various embodiments, 50-250 µL of a nasal composition in accordance with the present disclosure may be sprayed once or twice or more into each nostril, up to six times or more per day, as frequently as daily, for each day the person in need of treatment exhibits common cold symptoms.

For example, a typical regimen comprises two sprays of a nasal composition in accordance with the present disclosure up each nostril at least once per day and up to about 10-times per day, each day as needed to reduce duration of a common cold or to reduce severity and/or duration of cold symptoms in a human exhibiting such symptoms as nasal congestion, runny nose, watery eyes, dry/scratching throat and/or sneezing.

In various embodiments, compositions in accordance with the present disclosure may be packaged into dispensing bottles and placed into a combination package with a pharmaceutical drug. For example, a nasal spray composition, formulated in accordance with the present disclosure, may be provided in a small, (e.g. 15-20 mL) dispensing spray bottle, and that bottle placed into a carton alongside a bottle containing a pharmaceutical drug composition, such as a bottle of aspirin, TYLENOL® or TAMIFLU® capsules. In this way, the human in need of treatment can self-administer the analgesic or antiviral capsules, in accordance to a written prescription or bottle label for example, and augment that analgesic or antiviral treatment with the nasal spray composition of the present disclosure.

In various embodiments, combination packages may comprise a carton having cellophane view windows such that all products packaged therein can be seen by the consumer. Also, use instructions may be provided on the carton, and/or as a separate insert, instructing the consumer on the combined usage of the products within the carton.

Exemplary Compositions and Methods of Use

Two pharmaceutical compositions and a placebo composition are set out in Table 2 below. The NS-1 and Placebo-1 compositions were packaged into non-aerosol nasal spray bottles for use in the clinical trials.

TABLE 2

Exemplary Nasal Spray Compositions

| Ingredients (wt. %) | Nasal Spray Compositions | | |
|---|---|---|---|
| | NS-1 | NS-2 | Placebo-1 |
| Plant Extracts | | | |
| L. operculata 10 wt. % extract, MT | 0.01 | 0.10 | — |
| S. officinale 3X extract | 0.01 | | |
| G. glauca 10 wt. % extract, MT | 0.01 | | |
| Pharmaceutically acceptable carrier | | | |
| Water | 96.70 | 96.70 | 98.985 |
| Hypromellose | 1.00 | 1.00 | — |
| Polysorbate 80 | 0.08 | 0.08 | 0.08 |
| Succinic acid | 0.35 | 0.25 | — |
| $Na_2HPO_4$ and $NaH_2PO_4$ | 1.19 | 1.19 | — |
| Glycine | 0.10 | 0.10 | — |
| Inhalant mixture (eucalyptol, eugenol and menthol) | 0.07 | 0.07 | 0.01[1] |
| Fragrance (2-phenylethanol) | 0.01 | 0.01 | 0.005 |
| Sodium chloride | 0.45 | 0.45 | 0.90 |
| Sweetener | — | 0.03 | — |
| Preservative (benzalkonium chloride 50% active) | 0.02 | 0.02 | 0.02 |
| Total | 100.00 | 100.00 | 100.00 |

Notes:
[1] Only eucalyptol was used as inhalant mixture in Placebo-1

The pharmaceutical compositions in Table 2, along with similar liquid/gel compositions formulated in accordance with the present disclosure having combinations of these types of ingredients, are typically batch-prepared in a kettle with addition of ingredients as appropriate and simple mixing until uniform. Compositions NS-1 and NS-2 typically had pH values of about 4 to about 5, and viscosities from about 500 to about 1,500 cps (spindle #3, 50 rpm, 25° C.). These compositions and other embodiments thereby can be thickened more or less to any degree as appropriate for a desired finished dosage form or to accommodate a particular dispenser or dosing regimen.

In various embodiments, a composition in accordance with the present disclosure, useful for reducing duration of common colds in humans and for reducing the severity or duration of cold symptoms exhibited by humans having a common cold, comprises: (a) L. operculata 10 wt. % extract (MT), S. officinale 3× extract and/or G. glauca 10 wt. % extract (MT); and (b) a pharmaceutically acceptable carrier.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and/or *G. glauca* 10 wt. % extract (MT) at about 0.001 wt. % to about 0.1 wt. %; (b) a pharmaceutically acceptable carrier, wherein each wt. % is based on the total weight of the composition.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a pharmaceutically acceptable carrier, wherein each wt. % is based on the total weight of the composition.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener; (c) an acid; (d) an alkaline agent; and (e) water, wherein each wt. % is based on the total weight of the composition. In various embodiments, this basic composition may further comprise a surfactant, an amino acid, an inhalant, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) an acid at about 0.01 wt. % to about 10 wt. %; (d) an alkaline agent at about 0.01 wt. % to about 10 wt. %; and (e) water, wherein each wt. % is based on the total weight of the composition. In various embodiments, this basic composition may further comprise a surfactant, an amino acid, an inhalant, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener; (c) a surfactant; (d) an acid; (e) an alkaline agent; and (f) water, wherein each wt. % is based on the total weight of the composition. In various embodiments, this basic composition may further comprise an amino acid, an inhalant, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) a surfactant at about 0.001 wt. % to about 10 wt. %; (d) an acid at about 0.01 wt. % to about 10 wt. %; (e) an alkaline agent at about 0.01 wt. % to about 10 wt. %; and (f) water, wherein each wt. % is based on the total weight of the composition. In various embodiments, this basic composition may further comprise an amino acid, an inhalant, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener; (c) a surfactant; (d) an acid; (e) an alkaline agent; (f) an inhalant; and (g) water, wherein each wt. % is based on the total weight of the composition. In various embodiments, this basic composition may further comprise an amino acid, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) a surfactant at about 0.001 wt. % to about 10 wt. %; (d) an acid at about 0.01 wt. % to about 10 wt. %; (e) an alkaline agent at about 0.01 wt. % to about 10 wt. %; (f) an inhalant at about 0.001 wt. % to about 1 wt. %; and (g) water, wherein each wt. % is based on the total weight of the composition. In various embodiments, this basic composition may further comprise an amino acid, a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener; (c) a surfactant; (d) an acid; (e) an alkaline agent; (f) an inhalant; (g) an amino acid; and (h) water, wherein each wt. % is based on the total weight of the composition. In various embodiments, this basic composition may further comprise a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) a surfactant at about 0.001 wt. % to about 10 wt. %; (d) an acid at about 0.01 wt. % to about 10 wt. %; (e) an alkaline agent at about 0.01 wt. % to about 10 wt. %; (f) an inhalant at about 0.001 wt. % to about 1 wt. %; (g) at least one amino acid at about 0.01 wt. % to about 10 wt. %; and (h) water, wherein each wt. % is based on the total weight of the composition. In various embodiments, this basic composition may further comprise a salt, a fragrance, a preservative, a drug active, and/or a sweetener.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a thickener at about 0.001 wt. % to about 10 wt. %; (c) a surfactant at about 0.001 wt. % to about 10 wt. %; (d) an acid at about 0.01 wt. % to about 10 wt. %; (e) an alkaline agent at about 0.01 wt. % to about 10 wt. %; (f) at least one inhalant at about 0.001 wt. % to about 1 wt. %; (g) optionally at least one amino acid at about 0.01 wt. % to about 10 wt. %; (h) optionally at least one salt at about 0.01 wt. % to about 1 wt. %; (i) optionally at least one fragrance at about 0.001 wt. % to about 1 wt. %; (j) optionally at least one sweetener at about 0.001 wt. % to about 1 wt. %; (k) optionally at least one of a preservative, ultraviolet inhibitor and antioxidant at about 0.001 wt. % to about 1 wt. %; (l) optionally a non-aqueous solvent or vehicle at about 0.001 wt. % to about 99 wt. %; and (m) remainder water, wherein each wt. % is based on the total weight of the composition. In various embodiments, said composition includes a drug active.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a cellulosic thickener at about 0.001 wt. % to about 10 wt. %; (c) a surfactant at about 0.001 wt. % to about 10 wt. %; (d) an acid at about 0.01 wt. % to about 10 wt. %; (e) an alkaline agent at about 0.01 wt. % to about 10 wt. %; (f) at least one inhalant at about 0.001 wt. % to about 1 wt. %; (g) optionally at least one amino acid at about 0.01 wt. % to about 10 wt. %; (h) optionally at least one salt at about 0.01 wt. % to about 1 wt. %; (i) optionally at least one fragrance at about 0.001 wt. % to about 1 wt. %; (j) optionally at least one sweetener at about 0.001 wt. % to about 1 wt. %; (k) optionally at least one of a preservative, ultraviolet inhibitor and antioxidant at about 0.001 wt. % to about 1 wt. %; (l) optionally a non-aqueous solvent or vehicle at about 0.001 wt. % to about 99 wt. %; and (m) remainder water, wherein each wt. % is based on the total weight of the composition. In various embodiments, said composition further includes a drug active.

In various embodiments, a composition in accordance with the present disclosure, useful for reducing duration of common colds in humans and for reducing the severity or duration of cold symptoms exhibited by humans having a common cold, comprises: (a) *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a cellulosic thickener at about 0.001 wt. % to about 10 wt. %; (c) a nonionic surfactant at about 0.001 wt. % to about 10 wt. %; (d) an organic acid at about 0.01 wt. % to about 10 wt. %; (e) at least one of a carbonate, sulfate, and phosphate totaling about 0.01 wt. % to about 10 wt. %; (f) at least one inhalant at about 0.001 wt. % to about 1 wt. %; (g) optionally one amino acid at about 0.01 wt. % to about 10 wt. %; (h) optionally at least one salt at about 0.01 wt. % to about 1 wt. %; (i) optionally at least one fragrance at about 0.001 wt. % to about 1 wt. %; (j) optionally at least one sweetener at about 0.001 wt. % to about 1 wt. %; (k) optionally at least one of a preservative, ultraviolet inhibitor and antioxidant at about 0.001 wt. % to about 1 wt. %; (l) optionally a non-aqueous solvent or vehicle at about 0.001 wt. % to about 99 wt. %; and (m) remainder water, wherein each wt. % is based on the total weight of the composition. In various embodiments, said composition further includes a drug active.

In various embodiments, a composition in accordance with the present disclosure, useful for reducing duration of common colds in humans and for reducing the severity or duration of cold symptoms exhibited by humans having a common cold, comprises: (a) at least one of *L. operculata* 10 wt. % extract (MT) at about 0.001 wt. % to about 0.1 wt. %, *S. officinale* 3× extract at about 0.001 wt. % to about 0.1 wt. %, and *G. glauca* 10 wt. % extract (MT) at about 0.001 wt. % to about 0.1 wt. %; (b) a cellulosic thickener at about 0.001 wt. % to about 10 wt. %; (c) a surfactant at about 0.001 wt. % to about 10 wt. %; (d) an organic acid at about 0.01 wt. % to about 10 wt. %; (e) at least one of a carbonate, sulfate, and phosphate totaling about 0.01 wt. % to about 10 wt. %; (f) at least one inhalant at about 0.001 wt. % to about 1 wt. %; (g) optionally at least one amino acid at about 0.01 wt. % to about 10 wt. %; (h) optionally at least one salt at about 0.01 wt. % to about 1 wt. %; (i) optionally at least one fragrance at about 0.001 wt. % to about 1 wt. %; (j) optionally at least one sweetener at about 0.001 wt. % to about 1 wt. %; (k) optionally at least one of a preservative, ultraviolet inhibitor and antioxidant at about 0.001 wt. % to about 1 wt. %; (l) optionally a non-aqueous solvent or vehicle at about 0.001 wt. % to about 99 wt. %; (m) remainder water, wherein each wt. % is based on the total weight of the composition. In various embodiments, the said composition further includes a drug active.

In various embodiments, a composition in accordance with the present disclosure, useful for reducing duration of common colds in humans and for reducing the severity or duration of cold symptoms exhibited by humans having a common cold, consists essentially of: (a) *L. operculata* 10 wt. % extract (MT), *S. officinale* 3× extract, and *G. glauca* 10 wt. % extract (MT), totaling about 0.001 wt. % to about 0.5 wt. %; (b) a cellulosic thickener at about 0.5 wt. % to about 1.5 wt. %; (c) a nonionic surfactant at about 0.01 wt. % to about 1 wt. %; (d) an organic acid at about 0.1 wt. % to about 1 wt. %; (e) a mixture of monobasic and dibasic phosphate salts totaling about 0.1 to about 2 wt. %; (f) a mixture of menthol, eucalyptol and eugenol totaling about 0.1 wt. % to about 1 wt. %; (g) an α-amino acid at about 0.05 wt. % to about 0.5 wt. %; (h) sodium chloride at about 0.1 wt. % to about 1 wt. %; and (i) remainder water, wherein each wt. % is based on the total weight of the composition. In various embodiments, the composition also includes 2-phenylethanol, optionally any one of a preservative, uv inhibitor and antioxidant, and optionally a sweetener. In various embodiments, said cellulosic thickener is hypromellose. In various embodiments, said composition further includes a drug active.

In various embodiments, a liquid nasal spray useful for reducing duration of common colds in humans and for reducing the severity or duration of cold symptoms exhibited by humans having a common cold, consists essentially of: (a) *L. operculata* 10 wt. % extract (MT), *S. officinale* 3× extract, and *G. glauca* 10 wt. % extract (MT), totaling about 0.001 wt. % to about 0.5 wt. %; (b) a cellulosic thickener at about 0.5 wt. % to about 1.5 wt. %; (c) a polyethoxylated sorbitan fatty acid ester at about 0.01 wt. % to about 1 wt. %; (d) a di-carboxylic organic acid at about 0.1 wt. % to about 1 wt. %; (e) a mixture of monobasic and dibasic phosphate salts totaling about 0.1 to about 2 wt. %; (f) a mixture of menthol, eucalyptol and eugenol totaling about 0.1 wt. % to about 1 wt. %; (g) glycine at about 0.05 wt. % to about 0.5 wt. %; (h) sodium chloride at about 0.1 wt. % to about 1 wt. %; and (i) remainder water, wherein each wt. % is based on the total weight of the composition. In various embodiments, the composition also includes 2-phenylethanol, optionally any one of a preservative, uv inhibitor and antioxidant, and optionally a sweetener. In various embodiments, said cellulosic thickener is hypromellose. In various embodiments, said composition further includes a drug active.

In various embodiments, a method for reducing duration of a common cold in a human comprises nasal administration of a therapeutically effective amount of a pharmaceutical composition comprising: (a) a mixture of *L. operculata* extract, *S. officinale* extract and *G. glauca* extract; (b) from about 0.001 wt. % to about 10 wt. % of a thickener; and (c) a pharmaceutically acceptable carrier comprising at least about 90 wt. % water, wherein each wt. % is based on the total weight of the composition. In various embodiments, said composition further comprises from about 0.01 wt. % to about 10 wt. % of an organic acid, and from about 0.01 wt. % to about 10 wt. % of an alkaline material. In various embodiments, said composition further comprises from about 0.001 wt. % to about 1 wt. % of an inhalant. In various embodiments, said composition further comprises from about 0.01 wt. % to about 10 wt. % of an amino acid. In various embodiments, said composition further comprises from about 0.001 wt. % to about 10 wt. % of a surfactant. In various embodiments, said composition further comprises at least one drug active. In various embodiments, said therapeutically effective amount comprises from about 50 µL to about 250 µL of said composition.

In various embodiments, a method for reducing duration of a common cold in a human comprises nasal administration of a therapeutically effective amount of a pharmaceutical composition consisting essentially of: (a) from about 0.001 wt. % to about 0.5 wt. % of a mixture of *L. operculata* 10 wt. % extract (MT), *S. officinale* 3× extract and *G. glauca* 10 wt. % extract (MT); (b) from about 0.5 wt. % to about 1.5 wt. % of a cellulosic thickener; (c) from about 0.01 wt. % to about 1 wt. % of a polyethoxylated sorbitan fatty acid ester; (d) from about 0.1 wt. % to about 1 wt. % of a di-carboxylic organic acid; (e) from about 0.1 to about 2 wt. % of a mixture of sodium monobasic and sodium dibasic phosphate salts; (f) from about 0.1 wt. % to about 1 wt. % of a mixture of menthol, eucalyptol and eugenol; (g) from about 0.05 wt. % to about 0.5 wt. % glycine; (h) from about 0.1 wt. % to about 1 wt. % sodium chloride; and (i) from about 90 wt. % to about 99 wt. % water, wherein each wt. % is based on the total weight of the composition. In various embodiments, the composition optionally includes 2-phenylethanol, optionally any one of a preservative, uv inhibitor and antioxidant, and optionally a sweetener. In various embodiments, said cellulosic thickener is hypromellose. In various embodiments, said composition further includes a drug active.

In various embodiments, a method for reducing the severity or duration of common cold symptoms in humans, which includes reducing severity of any one of nasal congestion, runny nose, watery eyes, dry/scratchy throat and sneezing, comprises nasal administration of a therapeutically effective amount of a pharmaceutical composition comprising: (a) a mixture of *L. operculata* extract, *S. officinale* extract and *G. glauca* extract; (b) from about 0.001 wt. % to about 10 wt. % of a thickener; and (c) a pharmaceutically acceptable carrier comprising at least about 90 wt. % water, wherein each wt. % is based on the total weight of the composition. In various embodiments, said composition further comprises from about 0.01 wt. % to about 10 wt. % of an organic acid, and from about 0.01 wt. % to about 10 wt. % of an alkaline material. In various embodiments, said composition further comprises from about 0.001 wt. % to about 1 wt. % of an inhalant. In various embodiments, said composition further comprises from about 0.01 wt. % to about 10 wt. % of an amino acid. In various embodiments, said composition further comprises from about 0.001 wt. % to about 10 wt. % of a surfactant. In various embodiments, said composition further comprises at least one drug active. In various embodiments, said therapeutically effective amount comprises from about 50 µL to about 250 µL of said composition.

In various embodiments, a method for reducing the severity or duration of common cold symptoms in humans, which includes reducing severity of any one of nasal congestion, runny nose, watery eyes, dry/scratchy throat and sneezing, comprises nasal administration of a therapeutically effective amount of a pharmaceutical composition consisting essentially of: (a) from about 0.001 wt. % to about 0.5 wt. % of a mixture of *L. operculata* 10 wt. % extract (MT), *S. officinale* 3× extract, and *G. glauca* 10 wt. % extract (MT); from about 0.5 wt. % to about 1.5 wt. % of a cellulosic thickener; from about 0.01 wt. % to about 1 wt. % of a polyethoxylated sorbitan fatty acid ester; from about 0.1 wt. % to about 1 wt. % of a di-carboxylic organic acid; from about 0.1 to about 2 wt. % of a mixture of sodium monobasic and sodium dibasic phosphate salts; from about 0.1 wt. % to about 1 wt. % of a mixture of menthol, eucalyptol and eugenol; from about 0.05 wt. % to about 0.5 wt. % glycine; from about 0.1 wt. % to about 1 wt. % sodium chloride; and from about 90 wt. % to about 99 wt. % water, wherein each wt. % is based on the total weight of the composition. In various embodiments, the composition optionally includes 2-phenylethanol, optionally any one of a preservative, uv inhibitor and antioxidant, and optionally a sweetener. In various embodiments, said cellulosic thickener is hypromellose. In various embodiments, said composition further includes a drug active.

In various embodiments, a method for reducing the intensity or bothersomeness of a common cold in humans comprises nasal administration of a therapeutically effective amount of a pharmaceutical composition comprising: (a) a mixture of *L. operculata* extract, *S. officinale* extract and *G. glauca* extract; (b) from about 0.001 wt. % to about 10 wt. % of a thickener; and (c) a pharmaceutically acceptable carrier comprising at least about 90 wt. % water, wherein each wt. % is based on the total weight of the composition. In various embodiments, said composition further comprises from about 0.01 wt. % to about 10 wt. % of an organic acid, and from about 0.01 wt. % to about 10 wt. % of an alkaline material. In various embodiments, said composition further comprises from about 0.001 wt. % to about 1 wt. % of an inhalant. In various embodiments, said composition further comprises from about 0.01 wt. % to about 10 wt. % of an amino acid. In various embodiments, said composition further comprises from about 0.001 wt. % to about 10 wt. % of a surfactant. In various embodiments, said composition further comprises at least one drug active. In various embodiments, said therapeutically effective amount comprises from about 50 µL to about 250 µL of said composition.

In various embodiments, a method for reducing the intensity or bothersomeness of a common cold in humans comprises nasal administration of a therapeutically effective amount of a pharmaceutical composition consisting essentially of: (a) from about 0.001 wt. % to about 0.5 wt. % of a mixture of L. operculata 10 wt. % extract (MT), S. officinale 3× extract, and G. glauca 10 wt. % extract (MT); from about 0.5 wt. % to about 1.5 wt. % of a cellulosic thickener; from about 0.01 wt. % to about 1 wt. % of a polyethoxylated sorbitan fatty acid ester; from about 0.1 wt. % to about 1 wt. % of a di-carboxylic organic acid; from about 0.1 to about 2 wt. % of a mixture of sodium monobasic and sodium dibasic phosphate salts; from about 0.1 wt. % to about 1 wt. % of a mixture of menthol, eucalyptol and eugenol; from about 0.05 wt. % to about 0.5 wt. % glycine; from about 0.1 wt. % to about 1 wt. % sodium chloride; and from about 90 wt. % to about 99 wt. % water, wherein each wt. % is based on the total weight of the composition. In various embodiments, the composition optionally includes 2-phenylethanol, optionally any one of a preservative, uv inhibitor and antioxidant, and optionally a sweetener. In various embodiments, said cellulosic thickener is hypromellose. In various embodiments, said composition further includes a drug active.

Human Trials

Abbreviations

Table 3 lists abbreviations and definitions of terms relevant to the human trials described herein.

TABLE 3

Abbreviations

| | |
|---|---|
| AE | Adverse Event |
| ANCOVA | Analysis of Covariance |
| ANOVA | Analysis of Variance |
| ATC | Anatomical Therapeutic Chemical [Classification System] |
| AUC | Area Under Curve |
| CFR | Code of Federal Regulations |
| CRO | Contract Research Organization |
| CTCAE | Common Terminology Criteria for Adverse Events |
| eCRF | Electronic Case Report Form |
| EDC | Electronic Data Capture |
| EOS | End of Study |
| EOT | End of Treatment |
| FDA | Food and Drug Administration |
| GCP | Good Clinical Practice |
| ICF | Informed Consent Form |
| ICH | International Conference on Harmonization |
| IP | Investigational Product |
| IRB | Institutional Review Board |
| MedDRA | Medical Dictionary for Regulatory Activities |
| MG | Milligram |
| mITT | Modified Intent-to-Treat |
| PI | Principal Investigator |
| PIN | Personal Identification Number |
| PP | Per Protocol (Population) |
| SAE | Serious Adverse Event |
| SAP | Statistical Analysis Plan |
| SD | Standard Deviation |
| SOC | System Organ Class |
| TEAE | Treatment Emergent Adverse Event |
| WHODD | World Health Organization Drug Dictionary |

Study Objectives

The primary objective of the human trials was to determine whether early intervention in naturally-acquired common colds with a nasal spray formulated in accordance with the present disclosure reduces the duration of illness.

A secondary objective was to compare the effects of an investigational nasal spray formulated in accordance with the present disclosure versus a placebo composition on: 1) intensity of colds symptoms measured as a daily end-of-day assessment for the Total Core Colds Symptom Score; 2) intensity of the individual core colds symptom scores; 3) area under the curve (AUC day vs. score) for intensity of the Total Core Colds Symptom Score; 4) AUC for the individual core colds symptom scores; 5) AUC for the "bothersomeness" of the Total Core Colds Symptom Score; 6) the most "bothersome" cold symptom on each study day; 7) "I had a cold today" as a single determinant of daily illness; and 8) reduction in the daily intent to treat the colds illness with OTC drugs over the course of the illness, (including what type of product the participant would have chosen to use had they treated on that day). Lastly, on exit from the study, an assessment of how intense their cold was overall was made, and a rating of the intensity and duration of their current cold compared to their typical cold.

Design and Treatment

A double blind, placebo controlled, parallel group, randomized study was used to evaluate the effect of pharmaceutical composition NS-1 (see Table 2) in accordance with the present disclosure on the duration of naturally-acquired common colds in healthy adult subjects. The study was conducted across (12) clinical study sites in the United States. The placebo composition used in the study was Placebo-1 (see Table 2).

In a self-limited illness such as the common cold, crossover designs are not possible. This study used a randomized, double-blind, placebo-controlled, parallel treatment design comparing NS-1 nasal spray and matching placebo-1 initiated early in a natural history of the common cold. Randomization and double-blind elements of the study design were employed to minimize bias in treatment group assignment and investigator/study personnel/subject bias, respectively, during the study.

The study was performed in a double-blind manner. All study drugs were supplied in identical opaque bottles similar in appearance. The contents of the bottles were similar in color, smell, taste, and appearance, thereby assuring double-blind conditions.

Subjects were screened to verify the presence of a naturally-acquired common cold that has commenced in the last 36 hours prior to screening. Subjects who met all of the entry criteria were randomized into one of two treatment groups (NS-1 and Placebo-1) on Day 0.1 of the Treatment Period. Subjects received a kit of study drug product containing two bottles, each with 17.5 ml liquid composition. The amount of study drug product in each bottle was sufficient for 30 doses, or 120 sprays (doses=5×/day×6 days) of treatment and about 7 extra sprays to allow for pump priming and volume sufficiency during the last doses. The particular sprayers used in the study dispensed approximately 140 µL per spray. The NS-1 or Placebo-1 was dispensed in the morning of Day-1, and was subsequently sprayed twice in each nostril 5 times daily, approximately every 3 hours during waking hours, for 6 days. Subjects took between 3-5 doses on Day 1 depending on the time of entry into the study. Staff instructed each subject in the proper use of the nasal spray product issued. Subjects were instructed to lean their head backwards slightly and to not attempt to blow their nose, or lean forward, to drain test materials from the nostrils during the study.

Subjects were given diaries to capture notation of their cold symptoms after randomization on Day 1. Diaries were completed once daily prior to the final evening dose of study treatment. The final dose of study treatment was administered on Day 6. However, subjects continued to complete their symptom diaries for an additional 3 days. Subjects returned for an end of study, follow-up visit on Day 10 (+3 Days).

Study Population

There were 226 subjects randomized (112 in the Investigational NS-1-treated group and 114 in the Placebo-1-treated group), 217 (96%) of whom completed the study. Subjects had to present with a naturally-acquired common cold and had to admit having and cold and had to preset with at least two of the Core Cold Symptoms including runny nose, nasal congestion, watery eyes, sneezing, and dry/scratchy throat. The safety population contained all 226 subjects, while the modified intent-to-treat (mITT) population contained 222 subjects and the per-protocol (PP) population contained 208 subjects. A total of 9 subjects withdrew from the study; 1 for withdrawal by subject (1 in the Placebo-1-treated group), 5 for lost to follow-up (4 in the Investigational NS-1-treated group and 1 in the Placebo-1-treated group), and 3 with a reason of "other" (3 in the Placebo-1-treated group). In all randomized subjects, the mean subject age was 36.4 years, with a range of 18 to 65 years. For gender, 55% of the subjects were female and 45% were male. 45% of subjects were of Hispanic or Latino ethnicity, with 50 Hispanic or Latino subjects in the NS-1-treated group and 51 Hispanic or Latino subjects in the Placebo-1-treated group. For race, 75% of the subjects were White, 20% were Black or African American, 3% were Asian, 1% were American Indian or Alaska Native, less than 1% were Native Hawaiian or Other Pacific Islander, less than 1% were Multi-Racial, and less than 1% were "Other."

Inclusion Criteria
1. Generally healthy males or females between the ages of 18 and 65;
2. Female subjects must be: a) postmenopausal, defined as amenorrhea for at least 2 years at Screening, b) surgically sterile (have had a hysterectomy or bilateral oophorectomy, tubal ligation, or otherwise be incapable of pregnancy), c) abstinent, or d) if sexually active and of childbearing potential, be practicing an effective method of birth control such as hormonal prescription oral contraceptives, progesterone implants or injections, contraceptive patch, intrauterine device, or male partner with a vasectomy. A double barrier method such as condoms, diaphragms, or cervical caps with spermicidal foam, cream, or gel may be used as a method of birth control. Women of childbearing potential must have a negative urine pregnancy test at Visit 1/Day 1 before the first dose of study treatment is administered;
3. Subject must sign an informed consent document before the initiation of any study-related procedures, thus indicating that he or she understands the purpose of all procedures required for the study and is willing to participate in the study;
4. Subject is willing to be compliant with study procedures, including completing the daily diary during the screening/baseline period and continuing to do so throughout the study;
5. Subject must be on a stable dose of allowable medication for at least one month at the time of the screening/baseline visit;
6. Based on the questionnaire completed by the subject during the screening visit on study day 1, they must document the presence of a colds illness as well as the presence of at least 2 of the core cold symptoms which include: runny nose, nasal congestion, watery eyes, sneezing, and dry/scratchy throat;
7. Based on subject recollection, cold symptoms must have started within the past 36 hours; and
8. Subjects willing, and not reticent, to use nasal sprays.

Exclusion Criteria
1. Any subject who professes to "never get or had a cold";
2. History of a respiratory infection, cold, or flu-like syndrome between within 14 days prior to entry, including flu-like syndrome which may be as a result of a flu vaccination;
3. History of chronic respiratory disease, including, but not restricted to, chronic bronchitis, asthma, COPD, lung disease, cancers, etc.;
4. History of allergic or atopic disease including, but not restricted to, seasonal and perennial rhinitis, nasal polyps, chronic sinusitis, recurrent or chronic otitis, etc. and non-atopic nasal conditions such as vasomotor rhinitis;
5. History of autoimmune disease, rheumatoid arthritis, endocrine diseases, including diabetes;
6. History of abuse of legal or illegal drugs, particularly cocaine and alcohol;
7. Current smoker or cessation of smoking within the last year;
8. History of a deviated septum, nasal surgery, retention cysts, swollen nasal turbinates, or obstructed nasal airway;
9. History of GERD (gastric reflux), Zollinger-Ellison syndrome, or chronic cough due to reflux;
10. Any of the following, if deemed to be clinically significant by the Investigator: sitting blood pressure after 5 minutes >140/90 mmHg; pulse rate >95 bpm; respiratory rate >18 bpm;
11. Body temperature (oral)>38.3° C. at screening;
12. History of allergy or hypersensitivity to aspirin;
13. History of chronic dry eye, dry mouth, or Sjogren's disease;
14. History of severe or untreated periodontal disease;
15. Oral or periodontal surgery within three months prior to entry;
16. Current oral aphthous ulcers (canker sores) or herpes simplex lesions (cold sores);
17. Use of nasal steroid sprays within one month of entry;
18. Use of oral steroids within one month of entry;
19. Use of oral or nasal antihistamines, oral decongestants, nasal decongestants, cough suppressants, mucolytics, ibuprofen, naproxen within 2 days of entry;
20. Use of narcotics, codeine, or prescription pain medicines within one week of entry;
21. Use of angiotensin converting enzyme (ACE) inhibitors to control blood pressure;
22. Any female of child-bearing age who admits to being pregnant or when administered a pregnancy test tests positive on entry;
23. Any female who is lactating or breast-feeding;
24. Any subject who is unwilling to use nasal sprays or admits a negative experience with nasal products;
25. Any individual currently participating in a clinical trial of a drug product, or has been in a clinical trial of a drug product in the last 30 days;
26. Any individual who works for a pharmaceutical or consumer healthcare company; and
27. Any illness judged by the investigator to be significant in the week prior to screening.

Study Drug Compliance and Exposure

There were 226 bottles dispensed and 218 bottles returned. 221 subjects recorded dose information in subject diaries. The mean (SD) compliances were 99% (4.9%) in the NS-1-treated group and 97% (10.9%) in the Placebo-1-treated group. One subject had less than 75% compliance in the NS-1-treated group and 4 subjects had less than 75% compliance in the Placebo-1-treated group. No subject had compliance that was above 125%.

Criteria for Evaluation of Efficacy and Safety

The primary efficacy variable in the study is duration of the cold episode as measured by the number of days subjects remain in the study prior to the first two consecutive days when they admit to not having a cold.

The primary efficacy variable was evaluated by the subjects as daily end-of-day assessments of whether the subject believed he/she was suffering from a cold on that day. Duration was calculated as the number of days from day 1 to one day prior to the first two consecutive days without a cold. For example, if a subject marked "no cold" today on the 4$^{th}$ and 5$^{th}$ days, then the duration of that subject's cold is calculated to be 3 days.

Table 4 below sets out hypothetical scenarios A-H and shows what the "Duration" (in days) would be given the various end-of-day assessments in each hypothetical scenario.

TABLE 4

Hypothetical Scenarios for Determining Duration of the Cold Episode

| Scenario | Treatment | | | | | | Post Treatment | | | Duration (days) |
| --- | --- | --- | --- | --- | --- | --- | --- | --- | --- | --- |
| | Day 1 | Day 2 | Day 3 | Day 4 | Day 5 | Day 6 | Day 7 | Day 8 | Day 9 | |
| A | — | — | — | — | — | — | — | — | — | 9 |
| B | — | — | — | — | — | — | — | — | X | 9 |
| C | — | — | — | — | — | — | — | X | X | 7 |
| D | — | — | — | — | — | — | X | X | | 6 |
| E | — | — | — | — | — | X | X | X | X | 5 |
| F | — | — | — | — | — | X | — | X | X | 7 |
| G | — | — | — | — | — | X | — | — | X | 9 |
| H | — | — | — | — | X | | X | X | X | 6 |

X denotes a day without a cold, — denotes a day with a cold, and a blank indicates no assessment The criterion for showing clinical superiority of NS-1 over Placebo-1 was at least 1-day difference between the treatments in duration of the cold episode.

Supportive analyses of the primary efficacy variable include: (1) Number of days subjects remain in the study prior to the first two consecutive days when the daily total core colds symptom score burden is ≤2; and (2) Number of days subjects remain in the study prior to the first two consecutive days when they admit to not having a cold and their daily total core colds symptom score burden is ≤2 on those same two consecutive days.

Upon exit from the study, intensity and bothersomeness of the cold was assessed overall, and the intensity and duration of the participant's current cold was rated and compared to the participant's typical cold.

Variables for Self-Assessment of Cold Symptoms

Subjects rated the intensity of each individual symptom that at times, or when taken together, define aspects of a cold's natural history. Their rating was done at the end of each study day just prior to taking the last dose of treatment medication for that day. This approach is essentially integrative in that it asked the subject to integrate their experience over the course of their waking day. It relied on recall and subjective averaging of symptoms over approximately 12-16 waking hours.

Each subject also rated the "bothersomeness" of each symptom experienced that day. The same rating scale that was employed to estimate the intensity of symptoms was used to assess the degree of "bothersomeness." "Bothersomeness" is an expression of how that symptom has priority, standing or ranking in a subject's daily perception of the impact of the cold on his/her life.

Each subject was asked to select the one symptom that was most "bothersome" for that day.

In addition to individual symptoms, the grouping of the five "core" symptoms of the common cold, which include a runny nose, nasal congestion, watery eyes, sneezing, and dry/scratchy throat, was considered a secondary efficacy variable. These are the predominate symptoms occurring in the first 6 days of any cold episode.

Secondary Efficacy Variables

1. Intensity of colds symptoms measured as a daily end-of-day assessment for the Total Core Colds Symptom Score (sum of "runny nose, nasal congestion, watery eyes, sneezing and dry/scratchy throat" symptom scores);
2. Intensity of the individual Core Colds Symptom Scores;
3. Area under the curve (AUC day vs. score) for intensity of the Total Core Colds Symptom Score;
4. AUC for intensity of the individual colds symptom scores;
5. AUC for the "bothersomeness" of the total Core Colds Symptom Score;
6. The most "bothersome" cold symptom of the day;
7. "I had a cold today" as a single determinant of daily illness; and
8. Reduction in the daily intent to treat the colds illness with OTC drugs over the course of the illness.

At the end of each day prior to the last dose of test product, subjects completed the daily symptom diary, where they were asked to evaluate their cold that day with the following questions:

(1) How would you describe the intensity of each of the following symtoms?

(2) Over the course of today, how "bothersome" was each of the symptoms listed below?

(3) Over the course of today, which ONE symptom was the most "bothersome"?

The symptoms to be assessed are as follows and were rated by each subject on a scale of 0 to 5:

Symptoms:
A. Nasal congestion
B. Runny nose
C. Watery eyes
D. Dry/Scratchy throat
E. Sneezing
Scale:
0=Not present
1=Slight
2=Minimal
3=Moderate
4=Substantial
5=Intense At the end of each day, after answering the questions on intensity and "bothersomeness," subjects also responded to the following questions:

(1) Would you have treated your cold today had you not been in this study? [Y/N]

(2) If so, which of the 5 symptoms listed would you have treated today? [Check all that apply]

(3) Name a product, or products, you would have used today? [Open ended question]

Safety Variables

Safety was assessed by the frequency of adverse events (AEs), withdrawals due to AEs, and frequency of serious AEs (SAEs). Vital signs were also assessed in the study.

General Statistical Methods and Types of Analyses

Analysis Populations

Modified Intent-to-Treat Population (mITT)

The modified intent-to-treat (mITT) population included all randomized subjects who received at least one dose of study medication and who had at least one post-baseline diary assessment. Subjects were analyzed according to their randomized treatment assignment. The efficacy analyses were performed on the mITT population with Last Observation Carried Forward (LOCF) method for missing values. The efficacy variables could also have been analyzed utilizing the mITT population with observed data only (i.e., without LOCF) to assess sensitivity.

Per Protocol (PP) Population

PP population included all subjects in the mITT population who completed the study, with the exception of subjects with significant protocol deviations. Protocol deviations were assessed by the clinical team prior to database lock. The efficacy analyses were performed on the PP population with observed data only.

Safety Population

The safety population included all randomized subjects who received at least one dose of study medication. All safety analyses were performed on the safety population and subjects were analyzed according to the treatment received.

Sample Size and Power to Detect Significant Differences

With 110 subjects per treatment group for a total of 220 subjects, this study had approximately 90% power to detect a significant treatment difference between a test product (NS-1) and placebo (Placebo-1) in duration of a cold episode. A treatment difference of 1 day in duration of the cold episode is assumed with an approximated standard deviation of 2.3 days (two-sample t-test with two-sided $\alpha=0.05$; Mossad, 2003).

Efficacy Analysis

The continuous and ordinal efficacy variables collected at each visit (and day, where relevant) were summarized statistically with number of observations (n), mean, standard deviation, median, minimum and maximum. Qualitative variables were summarized statistically with counts and percentages. Where data were collected over time, both the observed data and change from the Screening Period (baseline) were summarized at each time point. All inferential tests were two-sided and were performed at the 5% level of significance, unless otherwise stated.

A Wilcoxon rank sums test was employed as the primary statistical inference method used to evaluate median duration of the cold episode, the primary efficacy variable. In addition, Kaplan-Meier curves were constructed. These methods were also used to evaluate the variables that support the primary efficacy variable.

Two-sample t-tests, Wilcoxon rank sums tests and ANCOVA models adjusting for baseline were employed for the continuous and ordinal secondary efficacy variables, as appropriate. For the ANCOVA models, a composition formulated in accordance with the present disclosure was compared to placebo. Pearson's chi-square tests or Fisher's exact tests (in the case of expected counts less than 5) was employed for inference testing of the qualitative secondary efficacy variables. Where appropriate, the change from baseline for each parameter was summarized using descriptive statistics.

The end-of-day total core colds symptom assessments were analyzed including all data across the 6-day treatment period, testing for a treatment effect using a generalized linear model that accounts for repeated measures with an unstructured correlation structure, including terms for day and the treatment by day interaction. The individual colds symptom assessments were analyzed in this same manner.

Results

The criterion for showing clinical superiority of the investigational nasal spray NS-1 over Placebo-1 was at least a 1-day difference (i.e., ≥1-day reduction) between the treatments in median duration of the cold episode.

Table 5 shows the targeted benefits achieved from use of the investigational nasal spray NS-1 rather than Placebo-1, and the corresponding p-values, with regards to duration of the cold episode. Nasal Spray NS-1 treatment demonstrated a clinically and statistically significantly shorter median duration of the cold episode compared to Placebo-1 (p=0.0196, Wilcoxon Rank Sum test), and a clinically and statistically significantly shorter mean duration of the cold episode compared to Placebo-1 (p=0.0232, Analysis of Covariance).

TABLE 5

Duration of the Cold Episode, mITT Population

| Parameter | NS-1 | Placebo-1 |
|---|---|---|
| n | 108 | 114 |
| Shorter Median Duration | YES | |
| p-value[1] | 0.0196 | |
| Shorter Mean Duration | YES | |
| p-value[2] | 0.0232 | |

Notes:
[1] p-value is calculated using Wilcoxon Rank Sum Test (NS-1 vs. Placebo-1)
[2] p-value is calculated using an ANCOVA model with Baseline (Pre-Dose) Total Core Colds Symptom Score as a covariate.

The daily and exit questionnaires collectively showed a statistically significant reduction in the severity of common cold symptoms including nasal congestion, runny nose, watery eyes, dry/scratchy throat, and sneezing. Additionally the results show significant results with respect to "bothersomeness," severity and length of the cold event.

Table 6 shows the pre-dose cold symptom questionnaire results for the question, "how would you describe the intensity of each of the following symptoms?" rated on the 0-5 scale for each symptom as discussed above, for each participant in the NS-1 and Placebo-1 groups (mITT population).

TABLE 6

Intensity of Symptoms Rated By Participant

| Symptom | NS-1 (n = 108) | Placebo-1 (n = 114) |
|---|---|---|
| Nasal Congestion | | |
| n | 108 | 114 |
| Mean (SD) | 3.0 (1.25) | 3.2 (1.17) |
| Median | 3.0 | 3.0 |
| Min, Max | 0, 5 | 0, 5 |
| Wilcoxon Rank Sum Test, NS-1 vs. Placebo-1 (p-value) | 0.1944 | |
| Runny Nose | | |
| n | 108 | 114 |
| Mean (SD) | 2.5 (1.38) | 2.5 (1.52) |
| Median | 3.0 | 3.0 |

TABLE 6-continued

Intensity of Symptoms Rated By Participant

| Symptom | NS-1 (n = 108) | Placebo-1 (n = 114) |
|---|---|---|
| Min, Max | 0, 5 | 0, 5 |
| Wilcoxon Rank Sum Test, NS-1 vs. Placebo-1 (p-value) | 0.7351 | |
| *Watery Eyes* | | |
| n | 108 | 114 |
| Mean (SD) | 2.2 (1.28) | 2.1 (1.47) |
| Median | 2.0 | 2.0 |
| Min, Max | 0, 5 | 0, 5 |
| Wilcoxon Rank Sum Test, NS-1 vs. Placebo-1 (p-value) | 0.2857 | |
| *Dry/Scratching Throat* | | |
| n | 108 | 114 |
| Mean (SD) | 2.6 (1.46) | 2.7 (1.47) |
| Median | 3.0 | 3.0 |
| Min, Max | 0, 5 | 0, 5 |
| Wilcoxon Rank Sum Test, NS-1 vs. Placebo-1 (p-value) | 0.4705 | |
| *Sneezing* | | |
| n | 108 | 114 |
| Mean (SD) | 2.5 (1.31) | 2.5 (1.28) |
| Median | 3.0 | 2.0 |
| Min, Max | 0, 5 | 0, 5 |
| Wilcoxon Rank Sum Test, NS-1 vs. Placebo-1 (p-value) | 0.9778 | |

Table 7 shows the "bothersomeness" results for the NS-1 and Placebo-1 groups. The results summarize the 0-5 scale ratings given by participants in answer to the question, "how bothersome" was each of the symptoms listed below?"

TABLE 7

The "Bothersomeness" of Symptoms Rated by Participant

| Symptom | NS-1 (n = 108) | Placebo-1 (n = 114) |
|---|---|---|
| *Nasal Congestion* | | |
| n | 108 | 114 |
| Mean (SD) | 3.0 (1.28) | 3.2 (1.28) |
| Median | 3.0 | 3.0 |
| Min, Max | 0, 5 | 0, 5 |
| Wilcoxon Rank Sum Test, NS-1 vs. Placebo-1 (p-value) | 0.1459 | |
| *Runny Nose* | | |
| n | 108 | 114 |
| Mean (SD) | 2.6 (1.44) | 2.5 (1.60) |
| Median | 3.0 | 2.5 |
| Min, Max | 0, 5 | 0, 5 |
| Wilcoxon Rank Sum Test, NS-1 vs. Placebo-1 (p-value) | 0.5983 | |
| *Watery Eyes* | | |
| n | 108 | 114 |
| Mean (SD) | 2.3 (1.35) | 2.0 (1.47) |
| Median | 2.0 | 2.0 |
| Min, Max | 0, 5 | 0, 5 |
| Wilcoxon Rank Sum Test, NS-1 vs. Placebo-1 (p-value) | 0.1251 | |
| *Dry/Scratching Throat* | | |
| n | 108 | 114 |
| Mean (SD) | 2.6 (1.53) | 2.7 (1.49) |
| Median | 3.0 | 3.0 |
| Min, Max | 0, 5 | 0, 5 |
| Wilcoxon Rank Sum Test, NS-1 vs. Placebo-1 (p-value) | 0.8171 | |

TABLE 7-continued

The "Bothersomeness" of Symptoms Rated by Participant

| Symptom | NS-1 (n = 108) | Placebo-1 (n = 114) |
|---|---|---|
| *Sneezing* | | |
| n | 108 | 114 |
| Mean (SD) | 2.5 (1.39) | 2.5 (1.36) |
| Median | 3.0 | 2.0 |
| Min, Max | 0, 5 | 0, 5 |
| Wilcoxon Rank Sum Test, NS-1 vs. Placebo-1 (p-value) | 0.9176 | |

Table 8 summarizes the questionnaire results for various additional questions as indicated.

TABLE 8

Additional Questions Answered by Participant

| Question | NS-1 (n =108) | Placebo-1 (n =114) |
|---|---|---|
| Over the course of today, which ONE symptom was the most "bothersome"? | | |
| Dry/scratchy throat | 24 (22.2%) | 34 (29.8%) |
| Nasal congestion | 49 (45.4%) | 58 (50.9%) |
| Runny Nose | 26 (24.1%) | 17 (14.9%) |
| Sneezing | 6 (5.6%) | 3 (2.6%) |
| Watery eyes | 3 (2.8%) | 2 (1.8%) |
| Chi-Square/Fisher's Exact Test (p-value) | 0.2481/0.2495 | |
| Would you have treated your cold today had you not been in this study? | | |
| No | 22 (20.4%) | 25 (21.9%) |
| Yes | 86 (79.6%) | 89 (78.1%) |
| Chi-Square/Fisher's Exact Test (p-value) | 0.7762/0.8697 | |
| If yes, which of the symptoms listed would you have treated today? (check all that apply) | | |
| Dry/scratchy throat | 33 (30.6%) | 45 (39.5%) |
| Nasal congestion | 59 (54.6%) | 65 (57.0%) |
| Runny Nose | 45 (41.7%) | 34 (29.8%) |
| Sneezing | 20 (18.5%) | 19 (16.7%) |
| Watery eyes | 17 (15.7%) | 9 (7.9%) |

Table 9 summarizes the results from the exist questionnaires.

TABLE 9

Exit Questionnaires

| Question | NS-1 (n = 108) | Placebo-1 (n =114) |
|---|---|---|
| How would you rate the intensity of this cold? | | |
| n | 108 | 112 |
| Mean (SD) | 2.9 (1.13) | 3.0 (1.14) |
| Median | 3.0 | 3.0 |
| Min, Max | 1, 5 | 1, 5 |
| Wilcoxon Rank Sum Test, NS-1 vs. Placebo-1 (p-value) | 0.4406 | |
| How would you rate the "bothersomeness" of this cold? | | |
| n | 108 | 114 |
| Mean (SD) | 2.7 (1.04) | 3.0 (1.60) |
| Median | 3.0 | 3.0 |
| Min, Max | 1, 5 | 1, 5 |
| Wilcoxon Rank Sum Test, NS-1 vs. Placebo-1 (p-value) | 0.0555 | |

TABLE 9-continued

Exit Questionnaires

| Question | NS-1 (n = 108) | Placebo-1 (n =114) |
|---|---|---|
| Was your cold better, worse, or about the same as past colds? | | |
| About the same | 44 (40.7%) | 55 (48.2%) |
| Better | 57 (52.8%) | 36 (31.6%) |
| Worse | 7 (6.5%) | 18 (15.8%) |
| Chi-Square/Fisher's Exact Test (p-value) | 0.0045/0.0044 | |
| Was your cold shorter, longer, or about the same length as past colds? | | |
| About the same | 29 (26.9%) | 32 (28.1%) |
| Longer | 6 (5.86) | 21 (18.4%) |
| Shorter | 73 (67.6%) | 56 (49.1%) |
| Chi-Square/Fisher's Exact Test (p-value) | 0.0047/0.0040 | |

As evident from Tables 5-9, nasal composition NS-1 reduced duration of a common cold when administered into the nostrils of participants exhibiting common cold symptoms. Nasal composition NS-1 also reduced the severity and duration of common cold symptoms in participants exhibiting such symptoms. Furthermore, nasal composition NS-1 reduced the intensity and bothersomeness of a common cold.

A therapeutically effective dosage, based on the clinical trials discussed herein, comprises from about 50 to about 250 µL of nasal spray composition. A therapeutically effective dosage regimen, based on the clinical trials discussed herein, comprises from about 50 to about 250 µL of nasal spray composition administered twice in each nostril 5 times daily, approximately every 3 hours for 6 days. In various embodiments, equivalent therapeutically effective dosages for other dosage forms (gels, pastes, pre-treated swabs, etc.) can be calculated such that the "active" ingredients (i.e., the ingredients excluding the pharmaceutically acceptable carrier) are dosed at similar levels as in the nasal spray dosage and regimen example discussed herein.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

What is claimed is:

1. A method for treating a common cold caused by Rhinovirus infection, said method comprising: nasally administering to a human in need thereof a therapeutically effective amount of a composition comprising: (a) from about 0.001 wt. % to about 0.5 wt. % of a mixture of *L. operculata* 10 wt. % extract (MT), *S. officinale* 3× extract and *G. glauca* 10 wt. % extract (MT); (b) from about 0.5 wt. % to about 1.5 wt. % of a cellulosic thickener; (c) from about 0.01 wt. % to about 1 wt. % of a surfactant; (d) from about 0.1 wt. % to about 1 wt. % of an organic acid; (e) from about 0.1 to about 2 wt. % of at least one alkaline material; (f) from about 0.001 wt. % to about 1 wt. % of an inhalant selected from the group consisting of eucalyptol, eugenol, menthol, camphor, and mixtures thereof; (g) from about 0.05 wt. % to about 0.5 wt. % of an amino acid; (h) from about 0.1 wt. % to about 1 wt. % sodium chloride; and (i) from about 90 wt. % to about 99 wt. % water, wherein each wt. % is based on the total weight of the composition.

2. The method according to claim 1, wherein said cellulosic thickener is hypromellose.

3. The method according to claim 1, wherein said surfactant is polysorbate 80.

4. The method according to claim 1, wherein said organic acid is succinic acid.

5. The method according to claim 1, wherein said at least one alkaline material is a mixture of sodium monobasic and sodium dibasic phosphate salts.

6. The method according to claim 1, wherein said inhalant is a mixture of eucalyptol, eugenol and menthol.

7. The method according to claim 1, wherein said amino acid is selected from the group consisting of glycine, L-lysine, and mixtures thereof.

8. The method according to claim 1, wherein said composition further comprises 2-phenylethanol at a level of about 0.001 wt. % to about 1 wt. %, based on the total weight of the composition.

9. The method according to claim 1, wherein said composition further comprises at least one drug active.

10. The method according to claim 1, wherein said therapeutically effective amount comprises from about 50 µL to about 250 µL of said composition administered twice in each nostril of the human in need of treatment thereof, 5 times daily, approximately every 3 hours during waking hours, for 6 days.

* * * * *